United States Patent
Tokiwa et al.

(10) Patent No.: US 7,754,864 B2
(45) Date of Patent: Jul. 13, 2010

(54) TYROSINASE ACTIVITY CONTROLLING AGENT, PROCESS FOR PRODUCING THE SAME AND EXTERNAL PREPARATION CONTAINING THE SAME

(75) Inventors: Yutaka Tokiwa, Tsukuba (JP); Masaru Kitagawa, Otsu (JP); Kenji Yoshino, Otsu (JP); Shusaku Yanagidani, Otsu (JP); Takao Raku, Tsukuba (JP); Tetsuzo Totani, Takatsuki (JP); Hiromi Shimakawa, Takatsuki (JP)

(73) Assignees: National Institute of Advanced Industrial Science and Technology, Tokyo (JP); Toyo Boseki Kabushiki Kaisha, Osaka (JP)

( * ) Notice: Subject to any disclaimer, the term of this patent is extended or adjusted under 35 U.S.C. 154(b) by 826 days.

(21) Appl. No.: 10/530,789

(22) PCT Filed: Oct. 10, 2003

(86) PCT No.: PCT/JP03/13018

§ 371 (c)(1),
(2), (4) Date: Apr. 8, 2005

(87) PCT Pub. No.: WO2004/033475

PCT Pub. Date: Apr. 22, 2004

(65) Prior Publication Data

US 2006/0052318 A1    Mar. 9, 2006

(30) Foreign Application Priority Data

| Oct. 10, 2002 | (JP) | ............................. 2002-297040 |
| Dec. 5, 2002 | (JP) | ............................. 2002-353403 |
| Apr. 23, 2003 | (JP) | ............................. 2003-117973 |
| Aug. 18, 2003 | (JP) | ............................. 2003-294543 |

(51) Int. Cl.
| C07G 3/00 | (2006.01) |
| C07H 15/00 | (2006.01) |
| C07H 17/00 | (2006.01) |
| A61K 31/70 | (2006.01) |
| A01N 43/04 | (2006.01) |
| A61K 8/18 | (2006.01) |
| A61Q 5/08 | (2006.01) |
| A61Q 19/02 | (2006.01) |

(52) U.S. Cl. .......................... 536/4.1; 536/18.5; 514/25; 514/844; 424/62

(58) Field of Classification Search .................... 514/25, 514/844; 536/4.1, 18.5; 424/62
See application file for complete search history.

(56) References Cited

U.S. PATENT DOCUMENTS 5,346,693 A    9/1994   Pilleux et al.

6,306,376 B1    10/2001    Philippe

FOREIGN PATENT DOCUMENTS

| EP | 0 477 927 A1 | 4/1992 |
| ES | 2 141 670 | 3/2000 |
| JP | 05-294820 | 11/1983 |
| JP | 04-182415 | 6/1992 |
| JP | 05-078222 | 3/1993 |
| JP | 05-137994 | 6/1993 |
| JP | 05-194181 | 8/1993 |
| JP | 05-320152 | 12/1993 |
| JP | 06-056815 | 3/1994 |
| JP | 06-305940 | 11/1994 |
| JP | 07-285874 | 10/1995 |
| JP | 07-316026 | 12/1995 |
| JP | 07-316048 | 12/1995 |
| JP | 08-009987 | 1/1996 |
| JP | 08-245680 | 9/1996 |
| JP | 09-271387 | 10/1997 |
| JP | 10-330218 | 12/1998 |
| JP | 11-071225 | 3/1999 |
| JP | 11-124318 | 5/1999 |
| JP | 11-189541 | 7/1999 |
| JP | 2001-151623 | 6/2001 |
| JP | 2001-158730 | 6/2001 |
| JP | 2001-278752 | 10/2001 |
| JP | 2001-288098 | 10/2001 |
| JP | 2001-316226 | 11/2001 |
| JP | 2001-322990 | 11/2001 |
| JP | 2002-003381 | 1/2002 |
| JP | 2002-047130 | 2/2002 |
| JP | 2002-114669 | 4/2002 |
| JP | 2002-114670 | 4/2002 |
| JP | 2002-275060 | 9/2002 |
| WO | WO 01/79241 A1 | 10/2001 |

OTHER PUBLICATIONS

Lozano, P, Daz, M, de Diego, T, Iborra, JL (2003) Ester Synthesis From Trimethylammonium Alcohols in Dry Organic Media Catalyzed by Immobilized Candida antarctica Lipase B, vol. 82, No. 3, p. 353-358.*

Gordon, A.J. and Ford, R.A. (1972) The Chemist's Companion, p. 447.*

Takido, M., Fukuhara, K., Yamanouchi, S., Takahashi (1983) Phlebotrichin, a Phenolic Compound from the Fresh Leaves of Viburnum phlebotrichum. Phytochemistry, vol. 22, No. 1, p. 223-225.*

Jun-ichi Kadokawa, et al., "Synthesis of Arbutin Derivative with a Kojic Acid Moiety," The Chemical Society of Japan No. 9 pp. 533-535 2001.

(Continued)

*Primary Examiner*—Shaojia Anna Jiang
*Assistant Examiner*—Scarlett Goon
(74) *Attorney, Agent, or Firm*—Knobbe Marten Olson & Bear LLP

(57) ABSTRACT

Disclosed is a tyrosinase activity controlling agent comprising, as an active ingredient, a compound that has tyrosinase inhibiting or promoting activity, an external preparation comprising the controlling agent, and a process for producing the compound.

14 Claims, 13 Drawing Sheets

OTHER PUBLICATIONS

Hideaki Matsuda, et al., "Pharmacological Studies on Leaf of *Arctostaphylos uva-ursi* (L.) Spreng. IV. Effect of 50% Methanolic Extract from *Arctostaphylos uva-ursi* (L.) SPRENG. (Bearberry Leaf) on Melanin Synthesis" Yakugaku Zasshi 112 (4) pp. 276-282 1992.

Takahisa Nishimura, et al., "Inhibitory Effects of Hydroquinone-*a*-glucoside on Melanin Synthesis," Yakugaku Zasshi 115(8) pp. 626-632 1995.

Youji Wachi, "Production of cosmetic ingredients by biotechnological process," Bio Industry 11(4), pp. 206-216 1994.

Shigehiro Hirano, "Some Functional Biofibers based on Chitin and Chitosan," Bio Industry 19(4) pp. 62-70 2002.

Nobuyoshi Nakajima, et al., "Lipase-catalyzed Synthesis of Arbutin Cinnamate in an Organic Solvent and Application of Transesterification to Stabilize Plant Pigments," Biosci. Biotech. Biochem. 61(11) pp. 1926-1928 1997.

C. J. Moye, "Non-Aqueous Solvents for Carbohydrates," Adv. Carbohydr. Chem. Biochem. 27, pp. 85-125 1972.

Sergio Riva, et al., "Protease-Catalyzed Regioselective Esterification of Sugars and Related Compounds in Anhydrous Dimethylformamide," J. Am. Chem. Soc. 110, pp. 584-589 1988.

Takahisa Nishimura, et al., "Purification and Some Properties of α-Amylase from *Bacillus subtilis* X-23 That Glucosylates Phenolic Compounds Such as Hydroquinone," Journal of Fermentation and Bioengineering vol. 78, No. 1 pp. 31-36 1994.

Ninfa Rangel Pedersen, et al., "Efficient transesterification of sucrose catalysed by the metalloprotease thermolysin in dimethylsulfoxide," FEBS Letters vol. 519, No. 1-3, pp. 181-184 May 22, 2002.

Nuria Armesto, et al., "Regioselective Enzymatic Acrylation of Methyl Shikimate. Infuluence of Acyl Chain Length and Solvent Polarity on Enzyme Specificity," J. Org. Chem., vol. 67, No. 14, pp. 4978-4981 Jul. 12, 2002.

Arto Liljeblad, et al., "Enzymatic methods for the preparation of enantiopure malic and aspartic acid derivatives in organic solvents," Tetrahedron: Asymmetry, vol. 10, pp. 4405-4415 1999.

Kohji Ishihara, et al., "A chemoenzymatic synthesis of aromatic carboxylic acid vinyl esters," Journal of Molecular Catalysis B: Enzymatic Vo. 7, pp. 307-310 1999.

L. Verotta, et al., "Polyphenolic Glycosides from African Proteaceae," Journal of Natural Products, vol. 62, No. 11, pp. 1526-1531 1999.

Nobuyoshi Nakajima, et al., "Lipase-Catalyzed Direct and Regioselective Acylation of Flavonoid Glucoside for Mechanistic Investigation of Stable Plant Pigments," Journal of Bioscience and Bioengineering, vol. 87, No. 1, pp. 105-107 1999.

Supplementary European Patent Office Search Report for Application No. EP03754072.

Takido M. et al. 1983 "Phlebotrichin, a phenolic compound from the fresh leaves of *Viburnum phlebotrichum*" Phytochemistry 22:223-225.

* cited by examiner

A

B

TYROSINASE ACTIVITY CONTROLLING AGENT, PROCESS FOR PRODUCING THE SAME AND EXTERNAL PREPARATION CONTAINING THE SAME

This application is the U.S. National Phase under 35 U.S.C. §371 of International Application PCT/JP2003/013018, filed Oct. 10, 2003, which claims priority to Japanese Patent Application No. 2002-297040, filed Oct. 10, 2002, No. 2002-353403, filed Dec. 5, 2002, No. 2003-117973, filed Apr. 23, 2003, and No. 2003-294543, filed Aug. 18, 2003. The International Application was not published under PCT Article 21(2) in English.

TECHNICAL FIELD

The present invention relates to a tyrosinase activity controlling agent comprising, as an active ingredient, a compound that has tyrosinase inhibiting or promoting activity; and to an external preparation comprising the controlling agent. The present invention further relates to a process for producing the compound.

Specifically, the present invention relates to a novel arbutin ester compound with tyrosinase inhibitory activity, a tyrosinase inhibitor comprising the compound as an active ingredient, and to an external preparation comprising the inhibitor. Further, the present invention relates to a tyrosinase inhibitor comprising undecylenic acid, a salt thereof or an ester derivative thereof as an active ingredient, and to an external preparation comprising the inhibitor. Furthermore, the present invention relates to a tyrosinase activity promoter comprising ascorbic acid or a derivative thereof as an active ingredient, and to an external preparation comprising the tyrosinase activity promoter. The present invention also relates to a process for producing an ester using an enzyme, the process being suitable for production of the tyrosinase inhibitor or promoter.

BACKGROUND ART

Among compounds with tyrosinase inhibitory activity, natural products, such as arbutin and kojic acid, are often used as whitening agents in the cosmetic and other fields (e.g., Journal of the Pharmaceutical Society of Japan, 112 (4), pp. 276-282, 1992; Journal of the Pharmaceutical Society of Japan, 115 (8), pp. 626-632, 1995; BIO INDUSTRY, 11 (4), 206, 1994; and Biosci. Biotech. Biochem., 61, 11, pp. 1926-1928, 1997). However, when used as external preparations for the skin, such as cosmetics, these compounds have the drawback in that they have high hydrophilicity and thus have poor skin absorption properties. Therefore, development of arbutin derivatives or other compounds with higher hydrophobicity have been desired. An arbutin derivative in which the phenol moiety has been esterified is known as a bleaching agent (Japanese Unexamined Patent Publication No. 1999-71225). Further, a compound obtained by converting the 6-position of arbutin into a hydroxy ester is known as a bleaching cosmetic preparation (Japanese Unexamined Patent Publication No. 1993-194181). Furthermore, a compound obtained by a transesterification reaction of arbutin and vinyl cinnamate using lipase to selectively esterify the 6-position of arbutin has been reported (Bioscience Biotechnology and Biochemistry, 61, 11, pp. 1926-1928, 1997). However, tyrosinase inhibitory activity of arbutin derivatives and skin-whitening effects based on the activity have not been established, and no arbutin derivatives with satisfactory effects have yet been obtained.

Undecylenic acid is a $C_{11}$ unsaturated fatty acid contained in the human skin, and plays an important role as a skin cleansing agent. Commercially, it is produced by pyrolysis of castor oil. Undecylenic acid and salts and derivatives thereof are known to have antifungal activity, and reportedly can be used as skin cleansing preparations (Japanese Unexamined Patent Publication No. 2002-114669). Recently, trehalose esters have been developed as cosmetic materials (Japanese Unexamined Patent Publications No. 2001-278752 and No. 1993-137994). However, no tyrosinase inhibitory activity of undecylenic acid, salts thereof and ester derivatives thereof has been reported.

Meanwhile, gray hair, an aging phenomenon, is known to be caused by a lack of melanin pigments being transferred to keratinocytes. Therefore, researchers have searched mainly for tyrosinase activity promoting components and melanogenesis promoting components in order to develop a hair graying inhibitor. Specifically, they have attempted to find hair graying inhibitory activity in extracts of natural products and various other substances, and to use various compounds as active ingredients. For example, Japanese Unexamined Patent Publication No. 1995-316048 proposed that ω-alkoxycarbonylalkylammonium, salts thereof, ω-alkoxycarbonylalkyltrialkylammonium and salts thereof are effective as melanogenesis promoters. Also proposed were adenosine derivatives (Japanese Unexamined Patent Publication No. 1994-305940) and dihydrolupeol derivatives (Japanese Unexamined Patent Publication No. 2002-3381). However, the safety of these chemical substances is not assured. Japanese Unexamined Patent Publication No. 1993-78222 proposed a hair graying inhibitor comprising an aqueous or ethanolic extract of Japanese coptis as an active ingredient. Japanese Unexamined Patent Publication No. 1995-285874 proposed a melanogenesis promoter comprising an essence of shellfish, such as cockles, green mussels, oysters or the like. Japanese Unexamined Patent Publication No. 1999-124318 proposed a hair graying inhibitor comprising, as an active ingredient, at least one member selected from *Equisetum arvense* L., *Lonicera japonica* Thunb., *Plectranthus japonicus*, *Vitis vinifera* L., *Luffa cylindrica* Roem., *Sambucus nigra*, *Rucus aculeatus* L., *Zizyphus jujuba*, and extracts thereof. Japanese Unexamined Patent Publication No. 1995-316026 proposed a hair preparation comprising at least one melanogenesis promoting component selected from culture solutions and cell extracts of basidiomycetes of the families Tricholomataceae, Hydnaceae, Polyporaceae, Fistulinaceae, Mucronoporaceae, Helvellaceae, Strophariaceae and Agaricaceae. Japanese Unexamined Patent Publication No. 1999-189541 proposed that *Piper methysticum* and extracts thereof exhibit a melanogenesis promoting effect. Further, melanogenesis promoting effects have been confirmed in extracts of seaweeds of the genus *Spyridia* and *Dictyota dichotoma* (Japanese Unexamined Patent Publication No. 1998-330218), extracts of *Panax ginseng* C. A. Meyer, *Panax notoginseng*, *Salvia miltiorrhiza*, *Yucca elephantipes*, *Eriobotrya japonica* Lindley, *Lonicera japonica* and *Sarsaparilla* (Japanese Unexamined Patent Publication No. 2001-288098), and *Ficus carica*, *Morus alba* and extracts thereof (Japanese Unexamined Patent Publication No. 2002-47130). However, the production of plant or animal extracts has limitations in availability of the raw materials, and the extracts have drawbacks in that the raw material concentration is inconsistent, resulting in unreliable performance. Therefore, the development of a synthetic compound with sufficient tyrosinase activity promoting effect and melanogenesis promoting effect has been desired.

In the food industry, enzymatic esterification reactions applicable to the production of ester compounds as mentioned above have already been put into practice using hydrophobic alcohols and fatty acids as raw materials (Bioindustry, 19, pp. 62-71 (2002)). However, when a hydrophilic compound that is sparingly soluble in hydrophobic solvents is used as a raw material, the reaction results in a low yield and is not readily applicable to practical production processes. Japanese Unexamined Patent Publication No. 1996-245680 reported a process for producing a sucrose ester in octane, hexane or like organic solvent using an enzyme that is soluble in organic solvents. However, since sucrose is sparingly soluble in such solvents, the process does not produce a high yield. Carbohydrates and purine nucleosides are, however, highly soluble in DMSO, DMF, and like solvents. For example, sucrose dissolves in DMSO to a concentration of about 40% (Advance of Carbohydrate Chemistry and Biochemistry, 27, pp. 85-125 (1972)). Purine nucleosides, such as guanosine, dissolve in DMF containing 50% or more of DMSO. However, it has been assumed that use of aprotic organic solvents, such as DMF and DMSO, is generally liable to inactivate hydrolases, making it difficult to perform reactions (Japanese Unexamined Patent Publications No. 1997-271387 and No. 1996-9987). Therefore, an enzyme that shows high activity even in solvents in which hydrophilic compounds are highly soluble is sought. Hitherto, proteases derived from bacteria of the genera *Bacillus* and *Streptomyces* have been found as enzymes that show high activity in DMF or like solvent (Journal of American Chemical Society, 110, pp. 584-589 (1988)). However, no enzymes have been found so far which retain high activities in solvents capable of dissolving saccharides and nucleosides.

DISCLOSURE OF THE INVENTION

The present invention provides a tyrosinase activity controlling agent comprising, as an active ingredient, a compound with tyrosinase inhibiting or promoting activity; an external preparation comprising the activity controlling agent; and an esterification process usable for producing the compound. The present invention is described below in detail.

I. The first preferable embodiment of the present invention provides an arbutin ester compound that has a significantly higher tyrosinase inhibitory activity than arbutin, and that has improved skin absorption properties; and a production process therefor.

The inventors conducted extensive research and found that introducing a hydrophobic substituent to the 6-position of arbutin improves the inhibitory activity of arbutin. They carried out further research based on this finding and accomplished the present invention.

The present invention provides the following arbutin ester compounds, tyrosinase activity inhibitors, and external preparations, and processes for producing arbutin ester compounds.

1-1. An arbutin ester compound represented by formula (1):

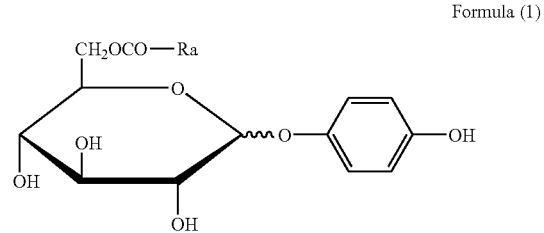

Formula (1)

wherein Ra is a hydrophobic group.

1-2. An arbutin ester compound according to item 1-1, which is represented by formula (2):

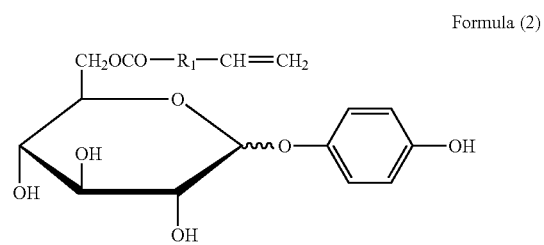

Formula (2)

wherein $R_1$ is a single bond, an alkylene group or an arylene group.

1-3. An arbutin ester compound according to item 1-1, which is represented by formula (3):

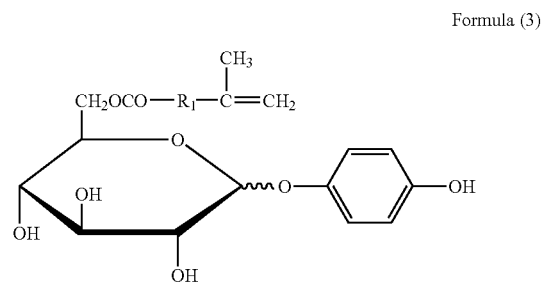

Formula (3)

wherein $R_1$ is a single bond, an alkylene group or an arylene group.

1-4. An arbutin ester compound according to item 1-1, which is represented by formula (4):

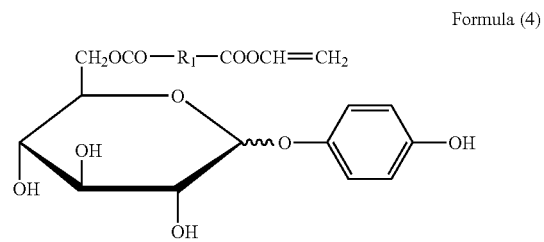

Formula (4)

wherein $R_1$ is a single bond, an alkylene group or an arylene group.

1-5. An arbutin ester compound according to item 1-1, which is represented by formula (5):

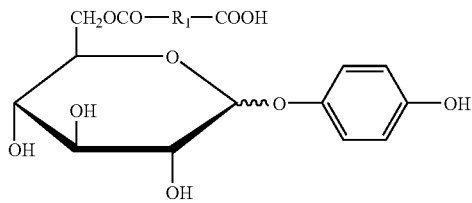

Formula (5)

wherein $R_1$ is a single bond, an alkylene group or an arylene group.

1-6. An arbutin ester compound according to item 1-1, which is represented by formula (6):

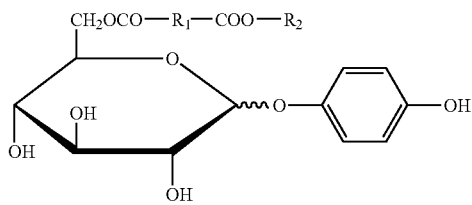

Formula (6)

wherein $R_1$ is a single bond, an alkylene group or an arylene group; and $R_2$ is an alkyl group or an aryl group.

1-7. An arbutin ester compound according to item 1-1, which is repr

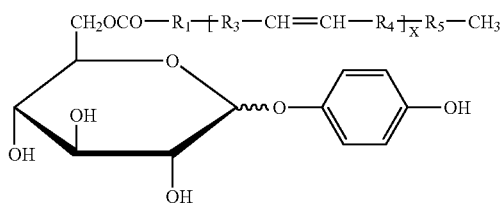

wherein $R_1$, $R_3$, $R_4$ and $R_5$ are each independently a single bond, an alkylene group or an arylene group; and X represents a number of repeating units and is 1 to 6.

1-8. An arbutin ester compound according to item 1-1, which is represented by formula (8):

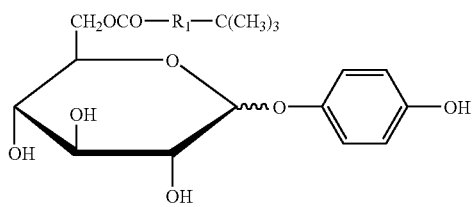

Formula (8)

wherein $R_1$ is a single bond, an alkylene group or an arylene group.

1-9. An arbutin ester compound according to item 1-1, which is represented by formula (9):

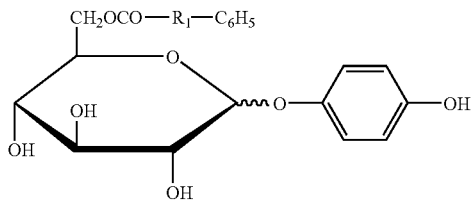

Formula (9)

wherein $R_1$ is a single bond, an alkylene group or an arylene group.

1-10. An arbutin ester compound according to item 1-1, which is represented by formula (10):

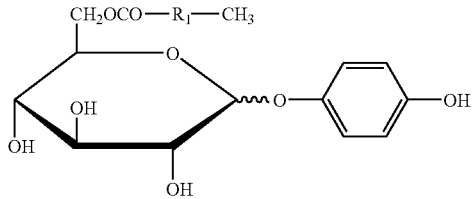

Formula (10)

wherein $R_1$ is a single bond, an alkylene group or an arylene group.

1-11. A tyrosinase inhibitor comprising, as an active ingredient, at least one of the arbutin ester compounds according to items 1-1 to 1-10.

1-12. An external preparation for the skin, comprising the tyrosinase inhibitor according to item 1-11.

1-13. A process for producing an arbutin ester compound, comprising the step of carrying out an esterification reaction of arbutin with a carboxylic acid compound represented by one of formulae (11) to (19); and specifically, a process for producing an arbutin ester compound represented by one of formulae (1) to (10), comprising the step of carrying out an esterification reaction of arbutin with a carboxylic acid represented by one of formulae (11) to (19):

$$A\text{-OCO}-R_1-CH=CH_2 \qquad \text{Formula (11)}$$

wherein A is hydrogen or a substituted or unsubstituted alkyl or vinyl group; and $R_1$ is a single bond, an alkylene group or an arylene group;

$$A\text{-OCO}-R_1-C(CH_3)=CH_2 \qquad \text{Formula (12)}$$

wherein A is hydrogen or a substituted or unsubstituted alkyl or vinyl group; $R_1$ is a single bond, an alkylene group or an arylene group;

$$A\text{-OCO}-R_1-COOCH=CH_2 \qquad \text{Formula (13)}$$

wherein A is hydrogen or a substituted or unsubstituted alkyl or vinyl group; and $R_1$ is a single bond, an alkylene group or an arylene group;

$$A\text{-OCO}-R_1-COOH \qquad \text{Formula (14)}$$

wherein A is hydrogen or a substituted or unsubstituted alkyl or vinyl group; and $R_1$ is a single bond, an alkylene group or an arylene group;

A-OCO—R₁—COO—R₂          Formula (15)

wherein A is hydrogen or a substituted or unsubstituted alkyl or vinyl group; R₁ is a single bond, an alkylene group or an arylene group; and R₂ is an alkyl group or an aryl group;

A-OCO—R₁—[—R₃—CH=CH—R₄—]ₓ—R₅—
           CH₃          Formula (16)

wherein A is hydrogen or a substituted or unsubstituted alkyl or vinyl group; R₁, R₃, R₄ and R₅ are each independently a single bond, an alkylene group or an arylene group; and X represents a number of repeating units and is 1 to 6.

A-OCO—R₁—C(CH₃)₃          Formula (17)

wherein A is hydrogen or a substituted or unsubstituted alkyl or vinyl group; and R₁ is a single bond, an alkylene group or an arylene group;

A-OCO—R₁—C₆H₅          Formula (18)

wherein A is hydrogen or a substituted or unsubstituted alkyl or vinyl group; and R₁ is a single bond, an alkylene group or an arylene group;

A-OCO—R₁—CH₃          Formula (19)

wherein A is hydrogen or a substituted or unsubstituted alkyl or vinyl group; and R₁ is a single bond, an alkylene group or an arylene group;

1-14. The process according to item 1-13, wherein the esterification reaction is carried out in the presence of an enzyme catalyst.

1-15. The process according to item 1-13, wherein the esterification reaction is carried out in the presence of a chemical catalyst.

1-16. The process according to any one of items 1-13 to 1-15, wherein the esterification reaction is carried out while performing a dehydration treatment.

1-17. The process according to any one of items 1-13 to 1-16, wherein the step of carrying out the esterification reaction is followed by the steps of:

extracting and isolating unreacted carboxylic acid derivative(s) from the reaction mixture using a nonpolar organic solvent; and subsequently, adding excess water to extract and isolate unreacted arbutin and to precipitate the arbutin ester compound.

The first embodiment of the present invention is described below in detail.

The arbutin ester compound of the present invention is a compound obtained by introducing a hydrophobic group to the 6-position of arbutin, and specifically, encompasses the compounds represented by formulae (1) to (10).

The arbutin ester compound of the present invention can be produced by an esterification reaction of arbutin with a carboxylic acid compound. In the specification and in the claims, carboxylic acids, dicarboxylic acids and derivatives of carboxylic and dicarboxylic acids are sometimes referred collectively as "carboxylic acid compound(s)".

The production of the arbutin ester compound is described below in detail.

Compound of Formula (2)

The compound of formula (2) can be synthesized by reacting arbutin with a carboxylic acid or carboxylic acid derivative represented by formula (11):

A-OCO—R₁—CH=CH₂          Formula (11)

wherein A is hydrogen or a substituted or unsubstituted alkyl or vinyl group; and R₁ is a single bond, an alkylene group or an arylene group.

The alkylene group has 1 to 16, and preferably 2 to 8, carbon atoms. The structure thereof is not limited, and may be straight-chain, branched-chain, cyclic or any other structure. Specific examples of the alkylene group include methylene, ethylene and other straight-chain alkylene groups; ethyl ethylene, isopropylene and other branched-chain alkylene groups; etc. The arylene group encompasses a phenylene group and the like.

Examples of carboxylic acid derivatives represented by formula (11) include acrylic acid derivatives and 10-undecylenic acid derivatives.

Compound of Formula (3)

The compound of formula (3) can be synthesized by reacting arbutin with a carboxylic acid or carboxylic acid derivative represented by formula (12):

A-OCO—R₁—C(CH₃)=CH₂          Formula (12)

wherein A is hydrogen or a substituted or unsubstituted alkyl or vinyl group; and R₁ is a single bond, an alkylene group or an arylene group.

The alkylene group has 1 to 16, and preferably 2 to 8, carbon atoms. The structure thereof is not limited, and may be straight-chain, branched-chain, cyclic or any other structure. Specific examples of the alkylene group include methylene, ethylene and other straight-chain alkylene groups; ethyl ethylene, isopropylene and other branched-chain alkylene groups; etc. The arylene group encompasses a phenylene group and the like.

Examples of carboxylic acid derivatives represented by formula (12) include methacrylic acid derivatives.

Compound of Formula (4)

The compound of formula (4) can be synthesized by reacting arbutin with a carboxylic acid or dicarboxylic acid derivative represented by formula (13):

A-OCO—R₁—COOCH=CH₂          Formula (13)

wherein A is hydrogen or a substituted or unsubstituted alkyl or vinyl group; and R₁ is a single bond, an alkylene group or an arylene group.

The alkylene group has 1 to 16, and preferably 2 to 8, carbon atoms. The structure thereof is not limited, and may be straight-chain, branched-chain, cyclic or any other structure. Specific examples of the alkylene group include methylene, ethylene and other straight-chain alkylene groups; ethyl ethylene, isopropylene and other branched-chain alkylene groups; etc. The arylene group encompasses a phenylene group and the like.

Examples of dicarboxylic acid derivatives represented by formula (13) include compounds derived from oxalic acid, malonic acid, succinic acid, glutaric acid, adipic acid, pimelic acid, suberic acid, azelaic acid, sebacic acid, nonanedicarboxylic acid, dodecanedicarboxylic acid and other aliphatic dicarboxylic acids; and from (ortho-, meth- and para-)phthalic acids and other dicarboxylic acids. Specific examples of such compounds include divinyl adipate.

Compound of Formula (5)

The compound of formula (5) can be synthesized by reacting arbutin with a dicarboxylic acid or a derivative thereof represented by formula (14):

A-OCO—R₁—COOH          Formula (14)

wherein A is hydrogen or a substituted or unsubstituted alkyl or vinyl group; and $R_1$ is a single bond, an alkylene group or an arylene group.

The alkylene group has 6 to 21, and preferably 8 to 12, carbon atoms. The structure thereof is not limited, and may be straight-chain, branched-chain, cyclic or any other structure. Specific examples of the alkylene group include methylene, ethylene and other straight-chain alkylene groups; ethyl ethylene, isopropylene and other branched-chain alkylene groups; etc. The arylene group encompasses a phenylene group and the like.

Examples of dicarboxylic acids and derivatives thereof represented by formula (14) include suberic acid, azelaic acid, sebacic acid, nonanedicarboxylic acid, dodecanedicarboxylic acid and other aliphatic dicarboxylic acids; (ortho-, meta- and para-)phthalic acids and other dicarboxylic acids; and compounds derived from such dicarboxylic acids.

Compound of Formula (6)

The compound of formula (6) can be synthesized by reacting arbutin with a carboxylic acid or dicarboxylic acid derivative represented by formula (15):

A-OCO—$R_1$—COO—$R_2$  Formula (15)

wherein A is hydrogen or a substituted or unsubstituted alkyl or vinyl group; $R_1$ is a single bond, an alkylene group or an arylene group; and $R_2$ is an alkyl group or an aryl group.

The alkylene group has 1 to 16, and preferably 2 to 8, carbon atoms. The structure thereof is not limited, and may be straight-chain, branched-chain, cyclic or any other structure. Specific examples of the alkylene group include methylene, ethylene and other straight-chain alkylene groups; ethyl ethylene, isopropylene and other branched-chain alkylene groups; etc. The arylene group may be, for example, a phenylene group.

$R_2$ is an alkyl group or an aryl group. The alkyl group has 1 to 16, and preferably 2 to 8, carbon atoms. Specific examples thereof include methyl, ethyl and other straight-chain alkyl groups, and isopropyl and other branched-chain alkyl groups. The aryl group may be, for example, a phenyl group.

Examples of dicarboxylic acid derivatives represented by formula (15) include compounds derived from oxalic acid, malonic acid, succinic acid, glutaric acid, adipic acid, pimelic acid, suberic acid, azelaic acid, sebacic acid, nonanedicarboxylic acid, dodecanedicarboxylic acid and other aliphatic dicarboxylic acids; and from (ortho-, meta- and para-)phthalic acids and other dicarboxylic acids.

Compound of Formula (7)

The compound of formula (7) can be synthesized by reacting arbutin with a carboxylic acid or a derivative thereof represented by formula (16):

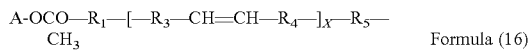

A-OCO—$R_1$—[—$R_3$—CH=CH—$R_4$—]$_X$—$R_5$—CH$_3$  Formula (16)

wherein A is hydrogen or a substituted or unsubstituted alkyl or vinyl group; $R_1$, $R_3$, $R_4$ and $R_5$ are each independently a single bond, an alkylene group or an arylene group; and X represents a number of repeating units and is 1 to 6.

The alkylene group has 1 to 21, and preferably 2 to 8, carbon atoms. The structure thereof is not limited, and may be straight-chain, branched-chain, cyclic or any other structure. Specific examples of the alkylene group include methylene, ethylene and other straight-chain alkylene groups; ethyl ethylene, isopropylene and other branched-chain alkylene groups; etc. The arylene group encompasses a phenylene group or the like.

Examples of carboxylic acids and derivatives thereof represented by formula (16) include decenoic acid, myristoleic acid, pentadecenoic acid, palmitoleic acid, hexadecatrienoic acid, heptadecenoic acid, heptadecadienoic acid, oleic acid, linolic acid, linolenic acid, γ-linolenic acid, octadecatetraenoic acid, eicosenoic acid, eicosadienoic acid, eicosatrienoic acid, eicosatetraenoic acid, arachidonic acid, eicosapentaenoic acid, docosenoic acid, docosadienoic acid, docosatetraenoic acid, docosapentaenoic acid, docosahexaenoic acid, tetracosenoic acid, and compounds derived from such carboxylic acids.

Compound of Formula (8)

The compound of formula (8) can be synthesized by reacting arbutin with a carboxylic acid or a derivative thereof represented by formula (17):

A-OCO—$R_1$—C(CH$_3$)$_3$  Formula (17)

wherein A is hydrogen or a substituted or unsubstituted alkyl or vinyl group; and $R_1$ is a single bond, an alkylene group or an arylene group.

The alkylene group has 1 to 16, and preferably 2 to 8, carbon atoms. The structure thereof is not limited, and may be straight-chain, branched-chain, cyclic or any other structure. Specific examples of the alkylene group include methylene, ethylene and other straight-chain alkylene groups; ethyl ethylene, isopropylene and other branched-chain alkylene groups; etc. The arylene group encompasses a phenylene group and the like.

Specific examples of carboxylic acid derivatives represented by formula (17) include compounds derived from pivalic acid and like compounds.

Compound of Formula (9)

The compound of formula (9) can be synthesized by reacting arbutin with a carboxylic acid or a derivative thereof represented by formula (18):

A-OCO—$R_1$—C$_6$H$_5$  Formula (18)

wherein A is hydrogen or a substituted or unsubstituted alkyl or vinyl group; and $R_1$ is a single bond, an alkylene group or an arylene group.

The alkylene group has 1 to 16, and preferably 2 to 8, carbon atoms. The structure thereof is not limited, and may be straight-chain, branched-chain, cyclic or any other structure. Specific examples of the alkylene group include methylene, ethylene and other straight-chain alkylene groups; ethyl ethylene, isopropylene and other branched-chain alkylene groups; etc. The arylene group encompasses a phenylene group and the like.

Specific examples of carboxylic acid derivatives represented by formula (18) include compounds derived from benzoic acid.

Compound of Formula (10)

The compound of formula (10) can be synthesized by reacting arbutin with a carboxylic acid or a derivative thereof represented by formula (19):

A-OCO—$R_1$—CH$_3$  Formula (19)

wherein A is hydrogen or a substituted or unsubstituted alkyl or vinyl group; and $R_1$ is a single bond, an alkylene group or an arylene group.

The alkylene group has 1 to 16, and preferably 2 to 8, carbon atoms. The structure thereof is not limited, and may be straight-chain, branched-chain, cyclic or any other structure. Specific examples of the alkylene group include methylene, ethylene and other straight-chain alkylene groups; ethyl ethylene, isopropylene and other branched-chain alkylene groups; etc. The arylene group encompasses a phenylene group and the like.

Specific examples of carboxylic acid derivatives represented by formula (19) include compounds derived from butyric acid, hexanoic acid, octanoic acid, decanoic acid, lauric acid, myristic acid, pentadecanoic acid, palmitic acid, heptadecanoic acid, stearic acid, arachidic acid, behenic acid and lignoceric acid.

It is preferable to carry out the above esterification reactions of arbutin with a compound represented by one of formulae (11) to (19) in the presence of an enzyme catalyst or chemical catalyst.

Usable enzyme catalysts include, for example, lipases, proteases, esterases and other known enzyme catalysts. Specific examples include *Pseudomonas cepacia*-derived lipases; *Candida anterctica*-derived lipases; *Bacillus subtilis*-derived proteases; *Streptomyces* sp.-derived proteases; etc. Among these, particularly preferable are *Candida antarctica*-derived lipase and *Bacillus subtilis*-derived protease.

Usable chemical catalysts include, for example, acids, alkalis, pyridine derivatives, and other known catalysts. Specific examples include p-toluenesulfonic acid, sodium alkoxides, titanium alkoxides, dimethylaminopyridine, hydrochloric acid, sulfuric acid, zinc acetate, pyridine, 4-pyrrolidinopyridine, dicyclohexylcarbamine, etc.

The above esterification reactions are preferably carried out in the presence of an enzyme catalyst, since such reactions have superior selectivity for the 6-position of arbutin. In particular, reactions using a *Candida anterctica*-derived lipase or *Bacillus subtilis*-derived protease are preferable.

When producing an arbutin ester using such an enzyme catalyst, the reaction temperature is 0 to 100° C., and preferably 30 to 50° C., and the reaction time is 1 to 340 hours, and preferably 24 to 170 hours. Usable solvents include dimethylformamide, dimethylsulfoxide, pyridine, acetone, dioxane and other solvents, which may be used singly or in combination. The carboxylic acid, dicarboxylic acid, or derivative thereof used as a starting material can also be employed as a solvent. The concentration of arbutin in the reaction mixture is 1 to 40 wt. %, and preferably 1 to 10 wt. %. The proportion of the enzyme to the reaction mixture is 0.1 to 20 wt. %, and preferably 0.1 to 1 wt. %. It is preferable to use the carboxylic acid, dicarboxylic acid or derivative thereof in an amount of about 0.5 moles to about 10 moles, preferably about 1 moles to about 5 moles, relative to 1 mole of arbutin.

When producing an arbutin ester using a chemical catalyst, the reaction temperature is 0 to 100° C., and preferably 40 to 50° C., and the reaction time is 1 to 48 hours, and preferably 1 to 24 hours. Usable solvents include dimethylformamide, dimethylsulfoxide, pyridine, acetone and dioxane, which may be used singly or in combination. The concentration of arbutin in the reaction mixture is 1 to 40 wt. %, and preferably 1 to 10 wt. %. The proportion of the chemical catalyst to the reaction solvent is 0.1 to 5 wt. %, and preferably 0.1 to 1 wt. %. It is preferable to use the carboxylic acid, dicarboxylic acid or derivative thereof in an amount of about 0.5 moles to about 10 moles, and in particular about 1 mole to about 5 moles, relative to 1 mole of arbutin.

In the present invention, the carboxylic acid, dicarboxylic acid, or derivative thereof for use as a starting material preferably has a free terminal carboxyl group. Compounds with a free terminal carboxyl group are advantageous in that they are inexpensive, and produce only water as a by-product of the esterification reaction. That is, a reaction using an ester compound as a starting material is likely to produce coloring matter, thus necessitating a purification treatment such as column chromatography, whereas a reaction using a compound with a free terminal carboxyl group does not cause such a problem.

The esterification reaction of arbutin with a compound with a free terminal carboxyl group, which produces water as a by-product, is preferably carried out while performing dehydration in order to efficiently perform esterification, since esterification reactions are reversible. The method for dehydration is not limited, and known methods can be suitably applied. Examples of applicable methods include dehydration under reduced pressure, dehydration in a stream of a dry inert gas, dehydration by selective adsorption of water on an inorganic substance, such as a molecular sieve. For small scale reactions, dehydration using molecular sieves is easy and preferable. The form of molecular sieve is not limited and it may be a powder, pellets or the like. The proportion of molecular sieve to be used is 0.1 to 50 wt. %, and preferably 1 to 20 wt. % in the total reaction mixture.

After the reaction, a known suitable separation and purification treatment is performed to separate, from the reaction product, the compound in which a hydrophobic group has been introduced to the 6-position of arbutin, thereby giving the arbutin ester compound of the present invention.

Usable separation and purification methods include known chromatographic methods such as high performance liquid chromatography, gel filtration chromatography, etc. The column type, mobile phase and other conditions can be suitably selected.

Also usable are liquid-liquid extraction, fractional precipitation based on solubility differences, and other separation methods. For example, unreacted carboxylic acid derivative(s) is extracted and separated from the esterification reaction mixture using a nonpolar organic solvent, and then excess water is added to extract and separate unreacted arbutin and, at the same time, to precipitate the arbutin ester compound. Such a process consisting of extraction, separation and precipitation is repeated as required, and thereafter the precipitate is collected to obtain the arbutin ester compound of the present invention.

Usable nonpolar solvents include, for example, cyclohexane, ethyl ether, petroleum ether, etc., among which cyclohexane is preferable.

"Excess water" means water in an amount, by weight, of about 20 times the amount of the arbutin compound used as a starting material.

A tyrosinase inhibitor can be obtained using as an active ingredient the arbutin ester compound represented by one of formulae (1) to (10) thus obtained.

The tyrosinase inhibitor comprises one or more of the arbutin ester compounds of formulae (1) to (10).

The tyrosinase inhibitor may be formulated, by a known process, from one or more of the arbutin ester compounds of formula (1) to (10), or from a mixture of the one or more of the compounds with a suitable carrier.

The tyrosinase inhibitor of the present invention can be added to cosmetic preparations, external preparations for the skin, medicines, foods, fish and shellfish feeds, etc., and can also be used for food treatment. For example, the tyrosinase inhibitor may be added to a cosmetic preparation to give a cosmetic product with skin whitening effect. Further, it can be added to foods or used for treating the surface of foods, in order to prevent discoloration of foods that are liable to discolor due to melanogenesis.

The tyrosinase inhibitor is also usable in an external preparation. In particular, it can be suitably used in an external preparation for the skin, and preferably an external preparation for skin whitening.

The external preparation for the skin of the present invention comprises one or more of the arbutin ester compounds represented by formulae (1) to (10).

The external preparation can be obtained by formulating a mixture of the tyrosinase inhibitor and a suitable carrier into a preparation by a known process.

The external preparation may contain various other ingredients generally used in external preparations, such as aqueous components, powdery components, moisturizers, surfactants, antiseptics, thickeners, ultraviolet absorbers, perfumes, etc.

The form of the external preparation may be, for example, an ointment, cream, milky lotion, liniment, lotion or the like.

The external preparation contains the arbutin ester compound in a tyrosinase-inhibiting effective amount. The proportion of the arbutin ester compound in the whole external preparation is about 0.001 wt. % to about 10% wt. %, and preferably about 0.005 wt. % to about 5 wt. %.

The external preparation is applied in a suitable amount, for example, to body parts, such as the face, neck, arm and hand, that are susceptible to or have spots, freckles or the like, or that are likely to be or have been tanned, once or several times daily.

The arbutin ester compound of the present invention has improved skin absorption properties due to the introduction of hydrophobic group, and has significantly higher tyrosinase inhibitory activity than arbutin. Moreover, the arbutin ester compound has antimicrobial activity against a wide variety of microorganisms, presumably due to its sugar ester structure; radical eliminating capacity, presumably due to its phenolic hydroxyl group; and surface activating properties, presumably due to the hydrophobicity of the ester moiety and the hydrophilicity of the arbutin moiety.

Because of these characteristics, the arbutin ester compound of the present invention can be effectively used as an active ingredient of a tyrosinase inhibitor or of external preparations for the skin and other preparations, in the cosmetic, medical and other fields.

II. The second preferable embodiment of the present invention provides a tyrosinase inhibitor comprising, as an active ingredient, undecylenic acid, a salt thereof or a derivative thereof; and an external preparation comprising the tyrosinase inhibitor, and, in particular, a cosmetic preparation for skin whitening comprising the tyrosinase inhibitor.

The present inventors conducted extensive research and found that undecylenic acid, salts thereof and sugar esters thereof have tyrosinase inhibitory activity, and carried out further studies.

The present invention provides the following tyrosinase inhibitors and external preparations.

2-1. A tyrosinase inhibitor comprising undecylenic acid, salt(s) thereof, and/or ester derivative(s) thereof represented by formula (20):

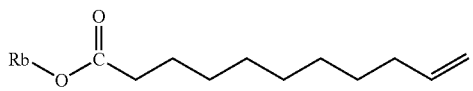

Formula (20)

wherein Rb is hydrogen or a sugar residue derived by removal of one hydroxyl group from a sugar.

2-2. The tyrosinase inhibitor according to item 2-1, wherein Rb is a sugar residue derived by removal of one hydroxyl group from a sugar.

2-3. The tyrosinase inhibitor according to item 2-1, which comprises the undecylenic acid and/or salt(s) thereof wherein Rb is hydrogen.

2-4. An external preparation comprising the tyrosinase inhibitor according to any one of items 2-1 to 2-3.

2-5. The external preparation according to item 2-4, which is a cosmetic preparation for skin whitening.

The second embodiment of the present invention is described below in detail.

Undecylenic Acid, Salt Thereof or Derivative Thereof

Undecylenic acid and salts thereof are known.

Examples of salts of undecylenic acid include salts of undecylenic acid with sodium, potassium, lithium and other alkali metals; with calcium, magnesium and other alkaline earth metals; and with copper, diethanolamine, ammonium, dimethylamine, trimethylamine, 2-amino-2-methyl-1,3-propanediol, 2-amino-2-methyl-1-propanol, stearyldimethylamine, etc.

Such salts can be prepared by mixing undecylenic acid with an alkali metal hydroxide, an alkaline earth metal hydroxide, another metal hydroxide or an amine in one or more solvents selected from water, alcohols (methanol, ethanol, isopropanol, butanol, etc.), THF, ether, acetonitrile, etc.

Rb is hydrogen or a sugar residue derived by removal of one hydroxyl group from a sugar. When Rb is a sugar residue, Rb—OH is a monosaccharide, disaccharide, trisaccharide, sugar alcohol or other sugar.

Examples of the sugar represented by Rb—OH include glucose, galactose, mannose, fructose, N-acetylglucosamine, N-acetylgalactosamine, ribose, arabinose, xylose, rhamnose and other monosaccharides; maltose, lactose, isomaltose, cellobiose, gentiobiose, sucrose, trehalose, isokojibiose, laminaribiose, nigerose, sambubiose, neohesperidose and other disaccharides; maltotriose, isomaltotriose, cellotriose, raffinose, gentiotriose and other trisaccharides; and glycerol, erythritol, xylitol, sorbitol, mannitol, inositol and other sugar alcohols. Preferred sugars include sucrose and trehalose.

The undecylenic acid ester of the present invention can be obtained by reacting undecylenic acid methyl ester, undecylenic acid ethyl ester or like ester with a sugar residue in the presence of an enzyme catalyst according to the method described in Japanese Unexamined Patent Publication No. 2000-65290 to thereby effect transesterification.

Examples of enzymes usable as the catalyst include alkaline proteases derived from *Bacillus* bacteria, lipases derived from *Candida antarctica*, etc.

A tyrosinase inhibitor can be obtained using, as an active ingredient, a compound selected from the group consisting of undecylenic acid, salts thereof, and ester derivatives thereof, or a mixture of at least two compounds selected from this group.

The tyrosinase inhibitor can be prepared by formulating at least one compound selected from undecylenic acid, salts thereof and ester derivatives thereof, alone or in combination with a suitable carrier, by a known process.

Further, the tyrosinase inhibitor can be added to cosmetic preparations for skin whitening, medicines, foods, fish and shellfish feeds, etc., or used for food treatment. The tyrosinase inhibitor inhibits tyrosinase activity to thereby suppress melanogenesis, and thus when added to a cosmetic preparation, provides a cosmetic product that has skin whitening effect.

Moreover, the tyrosinase inhibitor may be added to foods that are liable to discolor due to melanogenesis or used for treating the surface of such foods, to prevent discoloration. Undecylenic acid is a substance originally obtained from the skin, and its safety has been established. Skin whitening effect can be expected without safety concerns, by ingesting a food containing undecylenic acid or a salt thereof.

The tyrosinase inhibitor comprising, as an active ingredient, at least one member selected from the group consisting of undecylenic acid, salts thereof, undecylenic acid sugar esters represented by formula (20), can be used in an external preparation.

The external preparation can be preferably used for the skin, and especially as a cosmetic preparation for skin whitening, and can be produced by a known formulation process.

The external preparation may contain other generally used ingredients, such as aqueous components, powder components, moisturizers, surfactants, antiseptics, thickeners, ultraviolet absorbers, perfumes, etc.

The external preparation contains undecylenic acid, salt(s) thereof, and/or undecylenic acid sugar ester(s), in a tyrosinase inhibiting effective amount, i.e., in a proportion of usually about 0.001 wt. % to about 10 wt. %, preferably about 0.005 wt. % to about 5 wt. %, more preferably about 0.01 wt. % to about 3 wt. %, and especially preferably about 0.1 wt. % to about 1 wt. %, in the whole external preparation.

The form of external preparation is not limited, and may be, for example, an ointment, cream, milky lotion, liniment, lotion or other form.

The external preparation is applied in a suitable amount, for example, to body parts, such as the face, neck, arm and hand, that are susceptible to or have spots, freckles or the like, or that are likely to or have been tanned, once or several times daily.

The present invention was accomplished based on the finding that an ester of undecylenic acid with a disaccharide has a remarkably improved tyrosinase inhibitory activity, which is exhibited by a mechanism different from that of arbutin, and provides a tyrosinase inhibitor with such activity. Specifically stated, tyrosinase activity catalyzes a hydroxylation reaction of monophenol to 1,2-diphenol (catechol) and an oxidation reaction of catechol to o-quinone, and arbutin efficiently inhibits the hydroxylation reaction of monophenol, whereas the undecylenic acid sugar ester inhibits the oxidation reaction to catechol. That is, the undecylenic acid sugar ester has a different tyrosinase inhibitory mechanism from that of arbutin. More specifically, arbutin exhibits a higher inhibitory activity against a phenol substrate than against a catechol substrate as shown in FIG. 6, whereas the undecylenic acid sugar ester exhibits inhibitory activity against both catechol and phenol substrates as shown in FIG. 5. FIG. 9 illustrates these mechanisms.

With such activity, the tyrosinase inhibitor comprising, as an active ingredient, undecylenic acid, salt(s) thereof, and/or ester derivative(s) can be effectively used in an external preparation, and in particular in an external preparation for the skin and cosmetic preparation for skin whitening, in the cosmetic and medical fields.

III. The third preferable embodiment of the present invention provides a tyrosinase activity promoter comprising, as an active ingredient, ascorbic acid or a derivative thereof; and an external preparation comprising the tyrosinase activity promoter, and in particular an external preparation that has a remarkable effect for alleviating or preventing hair graying.

The present inventors found that ascorbic acid and ascorbic acid derivatives exhibit excellent tyrosinase activity promoting effects at low concentrations, and conducted extensive further studies.

The present invention encompasses the following tyrosinase activity promoters and external preparations comprising the tyrosinase activity promoters.

3-1. A tyrosinase activity promoter comprising ascorbic acid and/or ascorbic acid derivative(s) as an active ingredient.

3-2. A tyrosinase activity promoter according to item 3-1, wherein the ascorbic acid derivative(s) is at least one member selected from the group consisting of ascorbic acid fatty acid esters; ascorbic acid phosphoric acid esters, fatty acid esters thereof, and salts of the phosphoric acid esters and fatty acid esters; ascorbic acid glucosides and fatty acid esters thereof; and ascorbic acid sulfuric acid esters, fatty acid esters thereof, and salts of the sulfuric acid esters and fatty acid esters.

3-3. An external preparation comprising the tyrosinase activity promoter according to item 3-1 or 3-2.

3-4. An external preparation for the hair, comprising the tyrosinase activity promoter according to item 3-1 or 3-2, and preferably an external preparation for preventing or alleviating hair graying.

3-5. An external preparation for the skin, comprising the tyrosinase activity promoter according to item 3-1 or 3-2, and preferably an external preparation for darkening the skin or treating vitiligo of the skin.

3-6. An external preparation according to any one of items 3-3 to 3-5, wherein the total content of ascorbic acid and ascorbic acid derivative(s) is 0.00001 to 10 wt. % in the whole external preparation.

3-7. An external preparation according to any one of items 3-3 to 3-5, wherein the tyrosinase activity promoter comprises ascorbic acid as an active ingredient, and wherein the content of the ascorbic acid is 0.0001 to 1 wt. % in the whole external preparation.

3-8. An external preparation according to any one of items 3-3 to 3-5, wherein the tyrosinase activity promoter comprises, as an active ingredient, at least one compound selected from the group consisting of ascorbic acid phosphoric acid esters and ascorbic acid glucosides, and wherein the content of said at least one compound is 0.001 to 10 wt. % in the whole external preparation.

3-9. An external preparation according to any one of items 3-3 to 3-5, wherein the tyrosinase activity promoter comprises, as an active ingredient, at least one compound selected from the group consisting of fatty acid esters of ascorbic acid, fatty acid esters of ascorbic acid phosphoric acid esters, and fatty acids esters of ascorbic acid glucosides; and wherein the content of said at least one compound is 0.00001 to 0.1 wt. % in the whole external preparation.

The third embodiment of the present invention is described below in detail.

The tyrosinase activity promoter of the present invention comprises ascorbic acid and/or ascorbic acid derivative(s) as an active ingredient. In the tyrosinase activity promoter, ascorbic acid and ascorbic acid derivatives may be used singly or in combination.

Ascorbic acid is a water-soluble in vivo anti-oxidant, and is also called vitamin C. It exhibits its functions on various target molecules in various locations in vivo, or inside cells. Ascorbic acid encompasses L-ascorbic acid and D-ascorbic acid, of which L-ascorbic acid is used in the present invention.

Ascorbic acid derivatives usable in the present invention include those which have substituent(s) at one or more of the 2-, 3-, 5- and 6-hydroxyl positions, and which possess a tyrosinase activity promoting effect.

Specific examples of ascorbic acid derivatives include ascorbic acid fatty acid esters; ascorbic acid phosphoric acid esters, fatty acid esters thereof, and salts of the phosphoric acid esters and fatty acid esters; ascorbic acid glucosides and fatty acid esters thereof; ascorbic acid sulfuric acid esters, fatty acid esters thereof and salts of the sulfuric esters and fatty acid esters; etc. Particularly preferable are those producing ascorbic acid after being absorbed by the living body.

Of such ascorbic acid derivatives, the fatty acids, specifically those in ascorbic acid fatty acid esters, fatty acid esters of ascorbic acid phosphoric acid esters, fatty acid esters of ascorbic acid glucosides, and fatty acid esters of ascorbic acid sulfuric acid esters, are not limited in type and encompass saturated and unsaturated fatty acids and straight- and branched-chain fatty acids. The number of carbon atoms in each fatty acid moiety is not limited, and is usually 1 to 24, preferably 8 to 20, and more preferably 10 to 18.

Examples of ascorbic acid fatty acid esters include esters obtained by reacting a fatty acid with at least one of the hydroxyl groups at the 2-, 3-, 5- and 6-positions of ascorbic acid. Examples of such esters include ascorbic acid-6-palmitate, ascorbic acid-2,6-palmitate, ascorbic acid-6-stearate, etc.

Examples of ascorbic acid phosphoric acid esters include ascorbic acid-2-phosphate, which is obtained by esterification of the hydroxyl group at the 2-position of ascorbic acid with phosphoric acid.

Examples of salts of ascorbic acid phosphoric acid esters include alkali metal salts, alkaline earth metal salts and other salts of ascorbic acid phosphate esters. Specific examples include sodium ascorbic acid-2-phosphate, magnesium ascorbic acid-2-phosphate, etc.

Examples of fatty acid esters of ascorbic acid phosphoric acid esters include compounds obtained by further esterification of a hydroxyl group in an ascorbic acid phosphoric acid ester with a fatty acid, such as ascorbic acid-2-phosphoric acid-6-palmitate, ascorbic acid-2-phosphoric acid-6-laurate, ascorbic acid-2-phosphoric acid-6-stearate, etc.

Examples of salts of fatty acid esters of ascorbic acid phosphoric acid esters include sodium ascorbic acid-2-phosphate-6-palmitate, magnesium ascorbic acid-2-phosphate-6-laurate, etc.

Examples of ascorbic acid glucosides include ascorbic acid-2-glucoside in which glucose is linked to the hydroxyl group at the 2-position of ascorbic acid by a glycoside linkage.

Examples of fatty acid esters of ascorbic acid glucosides include compounds obtained by further esterification of an ascorbic acid glucoside with a fatty acid, such as ascorbic acid-2-glucoside-6-palmitate, ascorbic acid-2-glucoside-6-stearate, ascorbic acid-2-glucoside-6-laurate, etc.

Examples of ascorbic acid sulfuric acid esters include ascorbic acid-2-sulfate, which is obtained by esterification of the hydroxyl group at the 2-position of ascorbic acid with sulfuric acid.

Examples of salts of ascorbic acid sulfuric acid esters include alkali metal salts, alkaline earth metal salts and other salts of ascorbic acid sulfuric acid esters.

Examples of fatty acid esters of ascorbic acid sulfuric acid esters include compounds obtained by further esterification of a hydroxyl group of an ascorbic acid sulfuric acid ester with a fatty acid, such as ascorbic acid-2-sulfate-6-palmitate, ascorbic acid-2-sulfate-6-stearate, ascorbic acid-2-sulfate-6-laurate, etc.

Among these, ascorbic acid fatty acid esters, ascorbic acid phosphoric acid esters, fatty acid esters of ascorbic acid phosphoric acid esters, ascorbic acid glucosides, and fatty acid esters of ascorbic acid glucosides are preferable since they are highly stable and have excellent tyrosinase activity promoting effect.

The ascorbic acid and/or ascorbic acid derivative(s) for use as an active ingredient of the tyrosinase activity promoter of the present invention is used in an effective amount to thereby achieve excellent tyrosinase activity promoting effect.

Tyrosinase uses tyrosine as a substrate to catalyze the hydroxylation reaction of tyrosine and the oxidation reaction of produced DOPA. The ascorbic acid and/or ascorbic acid derivative serves as a hydrogen donor in the hydroxylation reaction, thereby promoting the tyrosinase activity.

The tyrosinase activity promoter comprising ascorbic acid and/or ascorbic acid derivative(s) is percutaneously absorbed, to reach the hair root region and act on melanocytes, thereby exhibiting excellent melanogenesis promoting effect.

With such a mechanism, the tyrosinase activity promoter comprising ascorbic acid and/or ascorbic acid derivative(s) as an active ingredient exhibits excellent melanogenesis promoting effects.

The tyrosinase activity promoter of the present invention can be obtained by formulating ascorbic acid and/or ascorbic acid derivative(s), alone or in combination with a suitable carrier, into a preparation by a known process.

Further, the tyrosinase activity promoter can be used as an ingredient of an external preparation. The external preparation can be produced by mixing the tyrosinase activity promoter and desired ingredients and/or suitable carrier by a known process.

The external preparation has an excellent tyrosinase activity promoting effect and/or excellent melanogenesis promoting effect, and can be used as, for example, an external preparation for the hair or skin. It can also be used as an external preparation for the treatment of Parkinson's disease, the preparation acting on melanocytes such as substantia *nigra*.

Specific examples of the external preparation for the hair include external preparations for preventing or alleviating hair graying or for browning the hair.

The type of the external preparation for the hair is not limited, and may be, for example, a shampoo, hair rinse, hair conditioner, hair pack, hair liquid, hair tonic, hair spray, hair restorer, hair dye, hair growth promoter or the like. The form of external preparation is not limited, and may be, for example, a liquid, milky lotion, cream, gel, solid or other form.

Specific examples of the external preparation for the skin include external preparations for treating vitiligo, or for tanning or darkening the skin.

The type of the external preparation for the skin is not limited and may be, for example, a lotion, milky lotion, cleansing cream, nourishing cream, makeup base cream, foundation, body lotion, hand cream, leg cream, facial cleansing preparation, body soap, body shampoo or the like. The form of the external preparation is not limited, and may be, for example, a lotion, liquid, cream, gel, milky lotion, solid or other form.

The external preparation may contain adjuvants that are effective for enhancing the efficacy of the tyrosinase activity promoter, or known additives. Such adjuvants and additives include, for example, liquid paraffin, vaseline and other hydrocarbons; carnauba wax, Japan wax and other waxes; olive oil, jojoba oil and other oils and fats; octadecyl palmitate, neopentyl glycol diisooctanate and other esters; stearic acid, palmitic acid and other higher fatty acids; cetyl alcohol, stearyl alcohol and other higher alcohols; nonionic, anionic, cationic and amphoteric surfactants; natural and synthetic perfumes and colors; parabens, chlorhexidine gluconate and other antiseptics; vitamin E, vitamin P and other vitamins; BHT and other antioxidants; benzophenone, aminobenzoic acid and other ultraviolet absorbers; ethanol, propanol and other alcohols; citric acid salts, acetic acid salts and other pH adjusting agents; medicinal ingredients suitable for the intended use of the preparation; etc.

The external preparation contains the tyrosinase activity promoter in a tyrosinase activity promoting effective amount, which is suitably adjusted according to the mode of use and types of the ingredients.

When the external preparation is used for the hair, the content of the tyrosinase activity promoter is about 0.00001 wt. % to about 10 wt. %, and preferably about 0.0001 wt. % to about 0.1 wt. %, in the whole external preparation. When the external preparation is used for the skin, the content of the tyrosinase activity promoter is about 0.00001 wt. % to about 10 wt. %, and preferably about 0.0001 wt. % to about 0.1 wt. %, in the whole external preparation.

When the tyrosinase activity promoter comprises ascorbic acid as an active ingredient, the content of the ascorbic acid is about 0.0001 wt. % to about 1 wt. %, preferably about 0.001 wt. % to about 1 wt. %, more preferably about 0.01 wt. % to about 1 wt. %, and even more preferably about 0.1 wt. % to about 1 wt. %, in the whole external preparation. Ascorbic acid is scarcely absorbed through the skin, and therefore, to adjust the intracellular ascorbic acid concentration to $10^{-4}$ M or lower, which is believed to be an effective amount, a suitable ascorbic acid concentration in the composition (tyrosinase activity promoter) as a whole is presumably about 0.0001 wt. % to about 1 wt. %.

When the tyrosinase activity promoter comprises, as an active ingredient, at least one compound selected from the group consisting of ascorbic acid phosphoric acid esters and ascorbic acid glucosides, the content of said at least one compound is 0.001 wt. % to about 10 wt. %, preferably about 0.01 wt. % to about 10 wt. %, more preferably about 0.01 wt. % to about 1 wt. %, and even more preferably about 0.1 wt. % to about 1 wt. %, in the whole external preparation. Ascorbic acid phosphoric acid esters and ascorbic acid glucosides have higher stability than ascorbic acid, and possess improved skin permeability and/or skin absorption properties compared with ascorbic acid. Thus, in order to adjust the intracellular ascorbic acid phosphoric acid ester/ascorbic acid glucoside concentration to $10^{-2}$ M to $10^{-4}$ M, which is believed to be an effective amount to exhibit activation effect, a suitable ascorbic acid phosphoric acid ester/ascorbic acid glucoside concentration in the composition (tyrosinase activity promoter) as a whole is presumably about 0.001 wt. % to about 10 wt. %.

When the tyrosinase activity promoter comprises, as an active ingredient, at least one compound selected from the group consisting of fatty acid esters of ascorbic acid, fatty acid esters of ascorbic acid phosphoric acid esters, and fatty acid esters of ascorbic acid glucosides, the content of said at least one compound is about 0.00001 wt. % to about 0.1 wt. %, preferably about 0.0001 wt. % to about 0.1 wt. %, more preferably about 0.001 wt. % to about 0.1 wt. %, and even more preferably about 0.01 wt. % to about 0.1 wt. %, in the whole external preparation. Fatty acid esters of ascorbic acid and ascorbic acid derivatives are highly stable and have considerably high skin permeability. Thus, in order to adjust the intracellular concentration of fatty acid ester(s) of ascorbic acid/ascorbic acid derivative(s) to $10^{-4}$ M or lower, which is believed to be an effective amount, a suitable concentration of fatty acid ester(s) of ascorbic acid/ascorbic acid derivative(s) in the composition (tyrosinase activity promoter) as a whole is about 0.00001 wt % to about 0.1 wt. %.

The present invention provides an tyrosinase activity promoter and external preparation that have excellent tyrosinase activity promoting activities or excellent melanogenesis promoting activities, using, as an active ingredient, ascorbic acid and/or an ascorbic acid derivative, which are highly safe and can be produced at low cost.

Hitherto, ascorbic acid and ascorbic acid derivatives have been used as melanogenesis inhibitors, but the present inventors found that ascorbic acid and ascorbic acid derivatives can be used as tyrosinase activity promoters and active ingredients of tyrosinase activity promoting pharmaceutical preparations and external preparations.

The tyrosinase activity promoter of the present invention is highly safe, can be produced at low cost, and exhibits excellent tyrosinase activating and melanogenesis promoting effects. Further, the external preparation comprising the tyrosinase activity promoter also exhibits excellent tyrosinase activating and melanogenesis promoting effects.

The tyrosinase activity promoter and external preparation comprising the tyrosinase activity promoter can be effectively used in the cosmetic, medical and other fields for the purpose of promoting tyrosinase activity or melanogenesis. For example, they can be used as external preparations for the hair to prevent or alleviate hair graying, or as external preparations for the skin to darken the skin or to treat vitiligo of the skin.

IV. The fourth preferable embodiment of the present invention provides a process for producing an ester using an enzyme in a solvent capable of dissolving saccharides and nucleosides.

The present inventors found that *Candida antarctica*-derived lipase type A is highly active in aprotic organic solvents. The present inventors further found that use of sucrose as a substrate enables a reaction with particularly high selectivity, and conducted extensive research based on these findings.

The present invention also provides the following processes for producing an ester.

4-1. The process for producing an ester, comprising esterifying hydroxyl-containing compound(s) with fatty acid(s) and/or derivative(s) thereof in the presence of *Candida antarctica*-derived lipase type A in an aprotic organic solvent.

4-2. The process according to item 4-1, wherein the aprotic organic solvent is selected from the group consisting of dimethylformamide, dimethylsulfoxide, and mixtures of dimethylformamide and dimethylsulfoxide.

4-3. The process according to item 4-1 or 4-2, wherein the hydroxyl-containing compound(s) is at least one member selected from the group consisting of saccharides, nucleosides, sugar alcohols and hydroxyl-containing amino acids.

4-4. The process according to item 4-3, wherein the hydroxyl-containing compound is a saccharide.

4-5. The process according to item 4-1, wherein the hydroxyl-containing compound is sucrose, and wherein the ester is a compound represented by formula (21):

Formula (21)

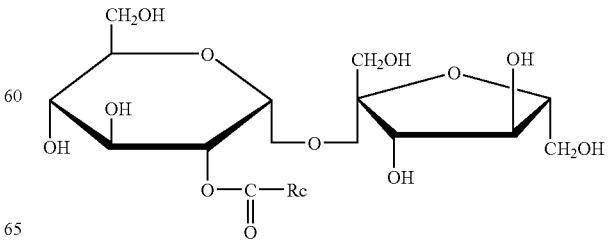

wherein Rc is a $C_{1-24}$ fatty acid residue.

The fourth embodiment of the present invention is described below in detail.

The process for producing an ester according to the fourth embodiment comprises esterifying hydroxyl-containing compound(s) with fatty acid(s) and/or derivative(s) thereof in the presence of *Candida antarctica*-derived lipase type A in an aprotic organic solvent.

As used in this embodiment, "esterifying" means synthesis of an ester, and encompasses esterification reactions and transesterification reactions. Specifically, esterifying encompasses reactions of carboxylic acids with alcohols (R'—COOH+R"—OH→R'—COO—R"); and reactions of esters with alcohols (R'—COO—R"+R'''—OH→R'—COO—R''').

Lipase

In the process of the present invention, *Candida antarctica*-derived lipase type A is used as an enzyme catalyst.

*Candida antarctica*-derived lipases are classified into types A and B. The present inventors found that lipase type A is an excellent enzyme catalyst that is highly active in aprotic organic solvents.

According to the present invention, even when a reaction is carried out using as a substrate a hydroxyl-containing compound, which is sparingly soluble in organic solvents, the product is obtained in high yield.

Lipase type A can be obtained from fermented lipase, for example, by gel filtration. Alternatively, lipase type A can be produced from the gene encoding lipase type A by recombinant DNA technology. Lipase type A is used in a proportion of about 0.1 wt. % to about 20 wt. %, and preferably about 0.1 wt. % to about 10 wt. %, to the total of the solvent and lipase.

The temperature for the reaction using lipase type A can be suitably selected, and is usually about 10° C. to about 100° C., and preferably about 30° C. to about 50° C.

Aprotic Organic Solvent

The process of the present invention is performed in an aprotic organic solvent.

The aprotic organic solvent is not limited in type, and may be, for example, dimethylformamide, dimethylacetamide, dimethylisopropylamide, formamide, dimethylsulfoxide, pyridine, N-methylpyrrolidone, N-methyl-2-pyrrolidinone, dipropylsulfoxide, or a mixed solvent thereof.

Among these solvents, dimethylformamide, dimethylsulfoxide, and mixed solvents thereof enable high production yields and thus are preferable. Dimethylsulfoxide is particularly preferable. The proportions of the solvents in the mixed solvent can be suitably selected, and the mixed solvent preferably contains at least 60%, and more preferably at least 80%, of dimethylsulfoxide.

Hydroxyl-Containing Compound

The hydroxyl-containing compound for use in the present invention is not limited as long as it contains at least one hydroxyl group. Examples of such compounds include saccharides, nucleosides, sugar alcohols, hydroxyl-containing amino acids, etc.

Examples of saccharides include natural and synthetic saccharides such as monosaccharides, oligosaccharides, polysaccharides and hydrolyzates thereof, etc. Also usable are substitution products and derivatives of such saccharides, such as amino sugars, thiosugars, uronic acid, etc. Further, solvates thereof are also usable.

Examples of monosaccharides include glucose, fructose, mannose, galactose, ascorbic acid, and other $C_{2-8}$, and preferably $C_{5-7}$, compounds.

Examples of oligosaccharides include trehalose and dihydrate thereof; sucrose, maltose, cellobiose, lactose and other disaccharides; raffinose and other trisaccharides; mannooligosaccharide, maltooligosaccharide and other oligosaccharides; etc.

Examples of polysaccharides include cellulose, starch, chitin, chitosan, hyaluronic acid, mannan, xylan, pullulan, etc.

Among these, preferable are monosaccharides and oligosaccharides, among which disaccharides are particularly preferable. Specifically, glucose, trehalose and sucrose are preferable, with sucrose being especially preferable.

Examples of nucleosides include compounds in which deoxyribose or ribose is bonded to adenosine, guanosine, cytosine, thymine or uracil, and derivatives of such compounds.

Examples of sugar alcohols include glycerol, erythritol, arabitol, xylitol, sorbitol, mannitol, inositol, etc.

Examples of hydroxyl-containing amino acids include serine, threonine, tyrosine, etc.

Such compounds can be used singly or in combination.

The concentration of hydroxyl-containing compound in the reaction solvent is about 0.01 M to about 1 M, and preferably about 0.1 M to about 0.5 M.

Fatty Acid or Derivative Thereof

The type of fatty acid or derivative thereof for use in the present invention can be suitably selected.

Examples of the fatty acid include saturated and unsaturated aliphatic monocarboxylic acids, dicarboxylic acids, and polycarboxylic acids with three or more carboxylic acid groups in the molecule. A suitable number of carbons in the fatty acid is usually 1 to 24, and preferably 6 to 18.

Examples of aliphatic monocarboxylic acids include caproic acid, sorbic acid, caprylic acid, capric acid, lauric acid, myristic acid, palmitoleic acid, palmitic acid, stearic acid, isostearic acid, oleic acid, linolic acid, linolenic acid, pentadecanoic acid, eicosanoic acid, docosanoic acid, decosenoic acid, arachidonic acid, ricinoleic acid, dihydroxystearic acid, etc. Among these, palmitic acid, stearic acid, caproic acid, caprylic acid and lauric acid are preferable.

Examples of dicarboxylic acids include adipic acid, sebacic acid, etc. Among these, saturated or unsaturated aliphatic dicarboxylic acids, and in particular adipic acid, are preferable, since polymerizable monomers can be obtained by converting such dicarboxylic acids into divinyl esters.

Examples of derivatives of fatty acids include fatty acid esters obtained by reaction of the above fatty acids with alcohols, acid anhydrides of fatty acids, etc. Examples of fatty acid esters include vinyl esters, lower alkyl esters, halogenated lower alkyl esters and the like of fatty acids. Among these, vinyl esters are preferable since vinyl groups act as excellent leaving groups in a transesterification reaction.

As used herein, "lower alkyl" means $C_{1-6}$ straight- or branched-chain alkyl, and "halogenated lower alkyl" means a lower alkyl substituted with at least one halogen (e.g., fluorine, chlorine or bromine) atom. Specific examples of derivatives of fatty acids include vinyl esters, methyl esters, ethyl esters, trifluoroethyl esters and trichloroethyl esters of the above-mentioned fatty acids, and divinyl esters of adipic acid and sebacic acid.

From the viewpoint of reactivity, particularly preferable are vinyl caproate, vinyl caprylate, vinyl laurate, vinyl myristate, vinyl palmitate, vinyl stearate, vinyl undecylate, vinyl oleate and divinyl adipate.

Such fatty acids and derivatives thereof may be used singly or in combination. Further, the fatty acids and derivatives thereof may be substituted with hydroxy, carbonyl, phenyl, halogen and/or other substituents.

The concentration of the fatty acid/derivative thereof is suitably selected, and is usually about 1 mole to 10 moles, and preferably about 1.2 moles to about 4 moles, per mole of the hydroxyl-containing compound.

Sucrose Ester

When sucrose is used as the hydroxyl-containing compound in the process for producing an ester, a compound is obtained in which the secondary hydroxyl group at the 2-position of sucrose is selectively esterified.

Specifically, when sucrose is esterified with a fatty acid or derivative thereof in the presence of *Candida antarctica*-derived lipase type A in an aprotic organic solvent, the compound of the following formula is obtained:

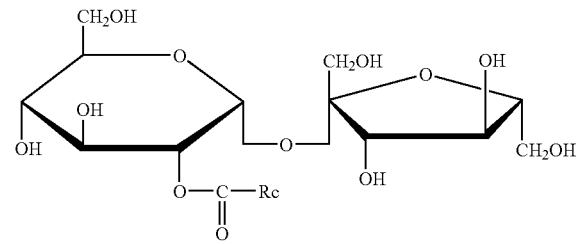

wherein Rc is a $C_{1-24}$ fatty acid residue.

The aprotic organic solvent can be suitably selected from the above-mentioned solvents, among which dimethylformamide, dimethylsulfoxide, and mixtures thereof are preferable, with dimethylsulfoxide being especially preferable.

The fatty acid or derivative thereof can be suitably selected as required from the above-mentioned and other fatty acids and derivatives thereof. Especially preferable from the viewpoint of reactivity are divinyl adipate, vinyl caproate, vinyl caprate, vinyl laurate, vinyl palmitate and vinyl stearate.

Sucrose esters used in practice are produced by processes using chemical catalysts, and are mixtures of mono-, di- and triesters. Moreover, in such sucrose esters, the primary hydroxyl groups at the 1'-, 6- and 6'-positions of sucrose are substituted by a fatty acid ester. Therefore, the sucrose esters have low hydrophilicity and are insufficiently soluble or emulsifiable in water. In contrast, according to the present invention, a monoester in which the hydroxyl group at the 2-position has been selectively esterified can be obtained in high yield. Further, a sucrose ester in which only the secondary hydroxyl group at the 2-position has been selectively esterified can be obtained with a high purity, without necessitating complicated procedures.

The sucrose ester in which the hydroxyl group in the 2-position has been selectively esterified, obtained by the process of the present invention, can be advantageously used as an emulsifier, surfactant or the like, in foods, cosmetics, shampoos, hair rinses, medicines, agricultural chemicals, cleaning agents, and other fields.

The process of the present invention is capable of effectively producing an ester, even when a highly water-soluble compound is used as a starting material. In particular, the process of the present invention is advantageously applicable to the production of esters which are difficult to produce synthetically and which are required to be produced by a selective reaction using an enzyme.

BRIEF EXPLANATION OF THE DRAWINGS

FIG. 12-B is a graph showing the sucrose ester conversion ratios of reactions carried out by adding *Candida antarctica*-derived lipase type B (CAL-B) to solutions of 0.125 M sucrose and 0.5 M divinyl adipate in mixed solvents consisting of DMF and DMSO in various proportions, followed by stirring at 30° C. for 7 days.

BEST MODE FOR CARRYING OUT THE INVENTION

Figure 1:
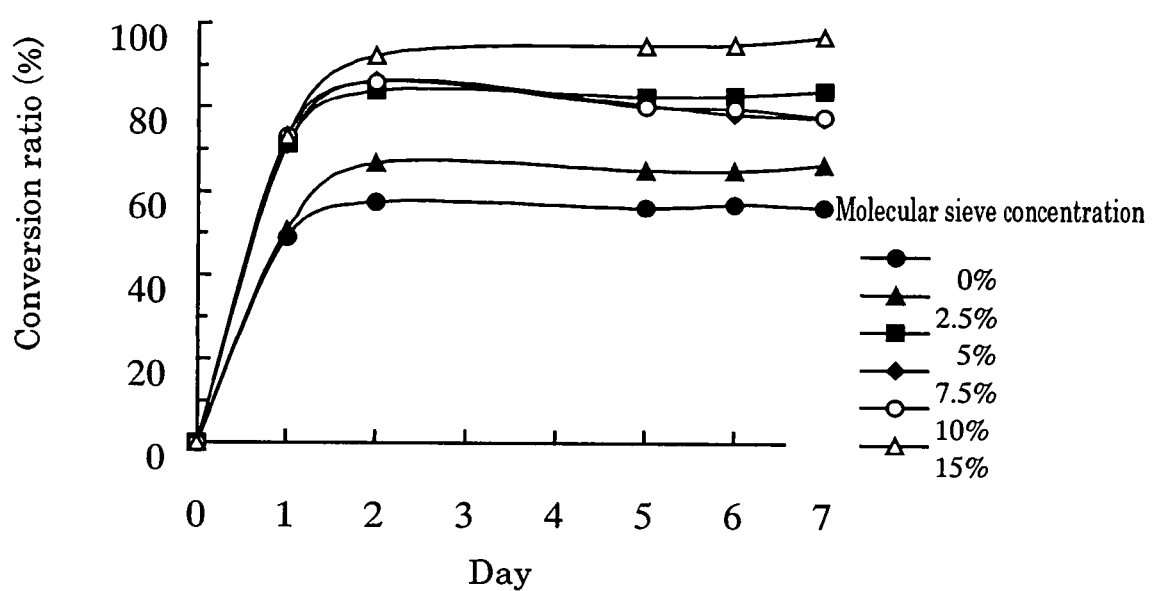
FIG. 1 is a graph showing the results of measuring the change over time in the arbutin conversion ratio (reaction ratio), in the production of an arbutin ester using molecular sieves, in which the molecular sieves are used at various concentrations. The analyses were performed using HPLC.

The following Examples and Comparative Examples are intended to illustrate the present invention in further detail, without in any way limiting the scope of the invention.

Example 1-1

Bacillus subtilis-derived protease (0.5 g, manufactured by Nagase ChemteX Corp.) was added to 72.6 ml of a dimethylformamide solution containing 6.8 g of arbutin, 21 g of 10-undecylenic acid vinyl ester and 3.8 g of water, followed by stirring at 30° C. and 130 rpm for 1 week. The conversion ratio was 80%. TLC analysis of the product revealed that substantially only a monoester was formed. The enzymatic reaction mixture was filtered to remove the enzyme powder, and the filtrate was concentrated under reduced pressure to remove DMF. The concentrate was added to a column packed with 100 g of silica gel, and eluted with chloroform:methanol (8:1). The product was collected and concentrated to give crystals of 6-O-(10-undecylenoyl)arbutin. The yield was 62%. $^{13}$C-NMR: δ 101.6 (C1), 76.4 (C2), 73.2 (C3), 70.1 (C4), 73.7 (C5), 63.4 (C6), 115.5, 117.7, 150.2 152.4 (phenol), 172.8 (C=O), 114.6, 138.9 (CH=CH$_2$), 24.4, 28.3, 28.5, 28.7, 33.2, 33.6 (CH$_2$) Anal. Calc'd for C$_{23}$H$_{34}$O$_8$ (438): C, 63.01; H, 7.76. Found: C, 63.16; H, 7.75.

Various aliphatic carboxylic acid vinyl esters were reacted with arbutin in the presence of Bacillus subtilis-derived protease in a similar manner. Table 1-1 shows the results.

TABLE 1-1

Arbutin ester syntheses using Bacillus subtilis-derived protease

| Aliphatic carboxylic acid vinyl ester | Product | Yield (%) |
|---|---|---|
| Vinyl acrylate | 6-O-acryloyl arbutin | 85 |
| Vinyl methacrylate | 6-O-methacryloyl arbutin | 91 |
| Divinyl adipate | 6-O-vinyladipoyl arbutin | 95 |
| Vinyl adipate | Arbutin 6-O-adipoyl acid ester | 75 |
| Vinyl methyl adipate | 6-O-methyladipoyl arbutin | 70 |
| Vinyl decenoate | 6-O-decenoyl arbutin | 92 |
| Vinyl oleate | 6-O-oleoyl arbutin | 82 |
| Vinyl pivalate | 6-O-pivaloyl arbutin | 75 |
| Vinyl benzoate | 6-O-benzoyl arbutin | 72 |
| Vinyl butyrate | 6-O-butayl arbutin | 86 |
| Vinyl laurate | 6-O-lauroyl arbutin | 80 |
| Vinyl stearate | 6-O-stearoyl arbutin | 73 |

Example 1-2

Arbutin (2.8 g) and divinyl adipate (9.5 g) were dissolved in 40.5 ml of pyridine, and 5 g of Streptomyces sp.-derived alkaline protease (manufactured by Toyobo Co., Ltd.) was added, followed by stirring at 30° C. and 130 rpm for 4 days. TLC analysis of the product revealed that only a monoester was produced. The enzymatic reaction mixture was filtered to remove the enzyme powder, and the filtrate was concentrated under reduced pressure to remove pyridine. The concentrate was added to a column packed with 100 g of silica gel, and eluted with hexane: acetic acid ethyl ester (4:1). The product was collected and concentrated to give crystals of 6-O-(vinyladipoyl) arbutin. The isolation yield was 85%. H-NMR: δ 1.556 (4H, m, —CH$_2$CH$_2$—), 2.320 (2H, m, —COCH$_2$—), 2.430 (2H, t, —CH$_2$CO—), 3.12-3.29 (3H, m, H-2,3,4), 3.508 (1H, m, H-5), 4.070 (1H, q, H-6), 4.310 (1H, dd, H-6), 4.640 (1H, dd, =CH$_2$), 4.675 (1H, d, H-1), 4.900 (1H, dd, =CH$_2$), 5.11-5.32 (3H, m, OH-2,3,4), 6.66 (2H, m, φ), 6.83 (2H, m, φ), 7.21 (1H, q, —CH=)

Further, reactions were carried out in DMF, DMSO or N-methyl-2-pyrrolidinone under otherwise the same conditions as above. The arbutin used as a starting material was rapidly esterified, and TLC analysis detected a monoester as the main product in these solvents. However, it was found that di-, tri- and tetraesters were also produced, unlike in pyridine.

Example 1-3

One gram of 4-pyrrolidinopyridine (manufactured by Wako Pure Chemical Ind. Ltd.) was added to 76.2 ml of a DMF solution containing 6.8 g of arbutin and 21 g of 10-undecylenic acid vinyl ester, followed by stirring at 80° C. and 130 rpm for 24 hours. TLC analysis of the product revealed that mono-, di-, tri- and polyesters were produced. The reaction mixture was concentrated under reduced pressure to remove DMF, added to a column packed with 100 g of silica gel, and eluted with chloroform:methanol (8:1). The produced monoester was collected and concentrated to give crystals of 6-O-(10-undecylenoyl) arbutin. The yield was 10%. $^{13}$C-NMR: δ 101.6 (C1), 76.4 (C2), 73.2 (C3), 70.1 (C4), 73.7 (C5), 63.4 (C6), 115.5, 117.7, 150.2 152.4 (phenol), 172.8 (C=O), 114.6, 138.9 (CH=CH$_2$), 24.4, 28.3, 28.5, 28.7, 33.2, 33.6 (CH$_2$) Anal. Calcd for C$_{23}$H$_{34}$O$_8$ (438): C, 63.01; H, 7.76. Found: C, 63.06; H, 7.81.

Various carboxylic acid vinyl esters were reacted with arbutin in the presence of 4-pyrrolidinopyridine in a similar manner. Table 1-2 shows the results.

TABLE 1-2

Arbutin ester syntheses using 4-pyrrolidinopyridine

| Aliphatic carboxylic acid vinyl ester | Product | Yield (%) |
|---|---|---|
| Vinyl acrylate | 6-O-acryloyl arbutin | 30 |
| Vinyl methacrylate | 6-O-methacryloyl arbutin | 22 |
| Divinyl adipate | 6-O-vinyladipoyl arbutin | 33 |
| Vinyl adipate | Arbutin 6-O-adipic acid ester | 12 |
| Vinyl methyl adipate | 6-O-methyl adipoyl arbutin | 22 |
| Vinyl decenoate | 6-O-decenoyl arbutin | 33 |
| Vinyl oleate | 6-O-oleoyl arbutin | 43 |
| Vinyl pivalate | 6-O-pivaloyl arbutin | 23 |
| Vinyl benzoate | 6-O-benzoyl arbutin | 22 |
| Vinyl butyrate | 6-O-butayl arbutin | 48 |
| Vinyl laurate | 6-O-lauroyl arbutin | 40 |
| Vinyl stearate | 6-O-stearoyl arbutin | 41 |

Example 1-4

Arbutin (0.3 g) and vinyl adipate (1 g) were dissolved in 4 ml of DMF, and 10 mg of dimethylaminopyridine was added thereto, followed by stirring at 80° C. for 3 hours. TLC analysis of the product revealed that mono-, di-, tri- and tetraesters were produced. The reaction mixture was concentrated under reduced pressure to remove DMF, added to a column packed with 100 g of silica gel, and eluted with chloroform:methanol (8:1). The monoester was collected and concentrated to give crystals of 6-O-(vinyladipoyl)arbutin. The yield was 21%.

Example 1-5

Arbutin (327 mg) and 10-undecylenic acid (885 mg) were dissolved in 4.0 ml of a 1,4-dioxane/DMSO (=9:1) mixed solvent in an Erlenmeyer flask. After adding 0.4 g of activated molecular sieves 4A, 40 mg of immobilized *Candida antarctica*-derived lipase (manufactured by Novozymes) was added, followed by stirring at 40° C. and 130 rpm for 1 week. The molecular sieve had been activated by a simple process using a microwave oven. Specifically, molecular sieves 4A placed in a flask had been heated in a microwave oven for 1 minute, and immediately thereafter, allowed to cool to room temperature under reduced pressure using a vacuum pump; this process was conducted three times. TLC analysis of the enzymatic reaction product revealed that only a monoester was produced. The enzymatic reaction mixture was filtered to remove the enzyme and molecular sieves, and then the filtrate was concentrated under reduced pressure. Methanol (4 ml) and water (2.5 ml) were added to the concentrate, and hexane (5 ml) was further added to extract unreacted undecylenic acid into the hexane layer. Such hexane extraction was carried out 6 times, and the aqueous layer was concentrated using an evaporator. After adding 8 mL of water to the concentrate to form a white precipitate, the supernatant liquid was removed by centrifugation. Such aqueous extraction was performed 3 times to remove DMSO and unreacted arbutin. The white precipitate was collected and dried under reduced pressure, to give 287 mg of powder.

TLC analysis of the purified product using 100% ethyl acetate confirmed that unreacted 10-undecylenic acid had been removed and that a single ester compound had been produced. The purified product was subjected to NMR analysis to thereby find that the it was the same compound as the ester obtained in Example 1-1, i.e., 6-O-(10-undecylenoyl) arbutin.

The yield of the ester was 91%. The process used in this Example does not involve purification with a silica gel column, and thus easy and simple.

Example 1-6

Arbutin (33 mg) and 10-undecylenic acid (89 mg) were dissolved in 4.0 ml of 1,4-dioxane in an Erlenmeyer flask. After adding 0 to 15 wt. % of activated molecular sieves 4A, 40 mg of immobilized *Candida anterctica*-derived lipase (manufactured by Novozymes) was added, followed by stirring at 40° C. and 130 rpm for 1 week. The molecular sieve had been activated by the same method as in Example 1-5. The change over time in arbutin conversion ratio was determined by HPLC analysis. The conditions for the HPLC analysis were as follows: Device; Shimazu LC-10, Column; TSK gel Amide-80, Mobile phase solvent; acetonitrile/water (=90:10), Flow rate; 1.0 ml, Detection; differential refraction.

FIG. 1 shows the results. The addition of molecular sieves, which act as a dehydrating agent, remarkably improved the arbutin conversion ratio (reaction ratio). The higher the concentration of molecular sieves, the higher the conversion ratio.

Example 1-7

Figure 2:
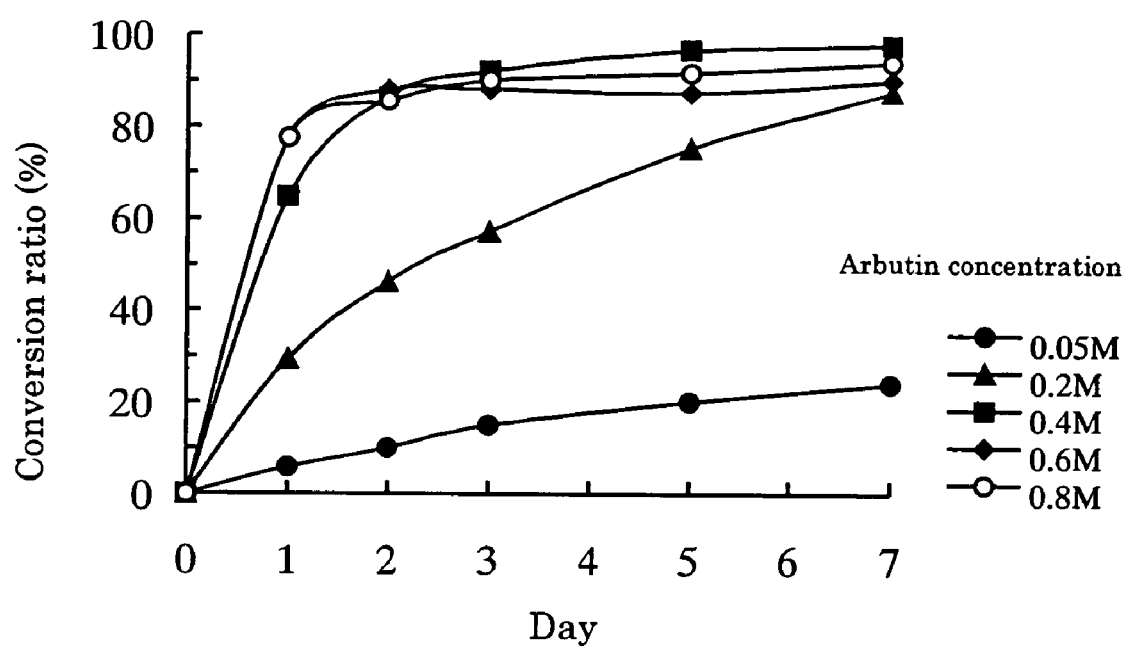
FIG. 2 is a graph showing the results of measuring the change over time in the arbutin conversion ratio (reaction ratio), in the production of an arbutin ester using molecular sieves, in which arbutin is used at various concentrations. The analysis was performed using HPLC.

Enzymatic reactions were performed in the same manner as in Example 1-6, except that arbutin is used in amounts of 55 mg to 872 mg (0.05 M to 0.8 M), and that 10-undecylenic acid was used in a molar amount four times that of arbutin. The changes over time in the arbutin conversion ratios were measured by HPLC analysis. FIG. 2 shows the results. The higher the concentration of arbutin, the higher the reaction rate. However, arbutin concentrations higher than 0.6 M did not further increase the reaction rate.

Evaluation 1: Evaluation of Tyrosinase Inhibitory Activity Using Proline

Figure 3:
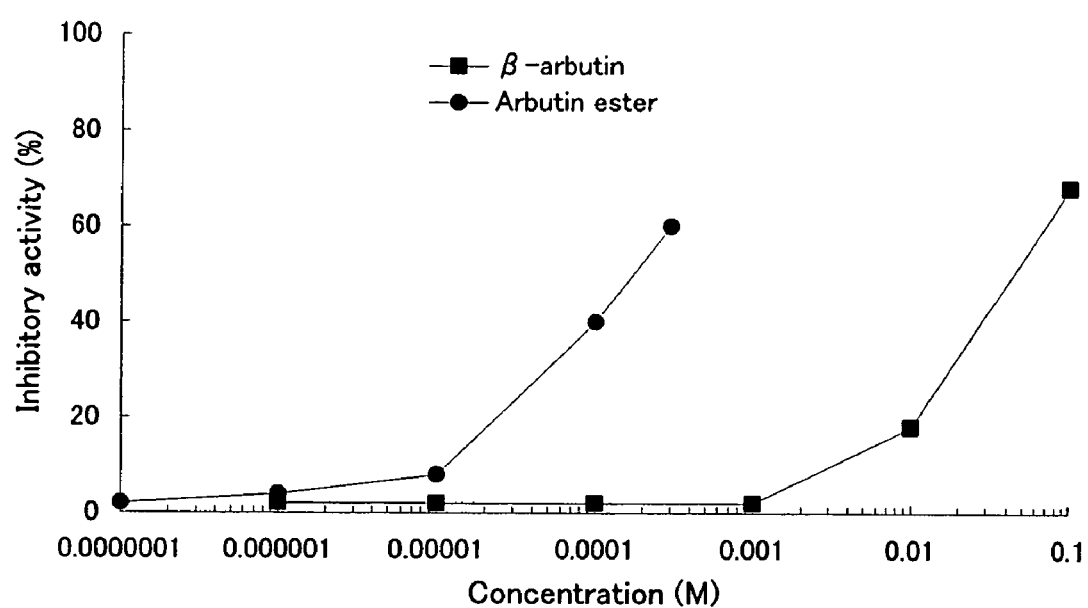
FIG. 3 is a graph showing the results of evaluating the inhibitory activity of arbutin and the arbutin ester compound obtained in Example 1 against mushroom-derived tyrosinase.

The tyrosinase inhibitory activity of the arbutin ester compound of the present invention was measured by a method using proline (Analytical Biochemistry, 179, 375-381, 1989). Forty microliters (μl) of 0.794 M L-proline dissolved in 0.1 M phosphate buffer at pH 7.5, 40 μl of 0.037 M 1,2-dihydroxybenzene, and 1.41 ml of one of the solutions of various concentrations of 6-O-(10-undecylenoyl) arbutin obtained in Example 1-1 were stirred in a cuvette for absorbance measurement. A solution (10 μl) of 350 μl/ml of tyrosinase (derived from mushroom, SIGMA) was added, and the absorbance change over time was determined with stirring for 10 seconds at 525 nm. This procedure was repeated except for using arbutin in place of 6-O-(10-undecylenoyl) arbutin. FIG. 3 shows the results.

FIG. 3 demonstrates that the arbutin compound obtained by esterifying the hydroxyl group at the 6-carbon of arbutin has a remarkably improved tyrosinase inhibitory activity over non-esterified arbutin.

Figure 4:
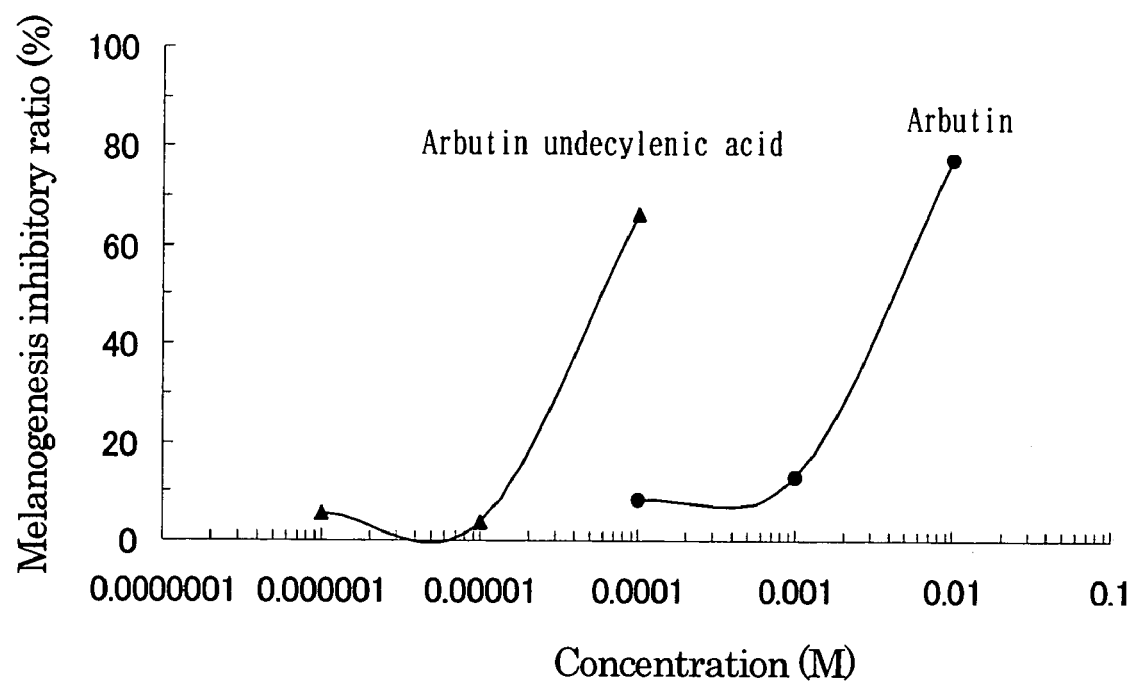
FIG. 4 is a graph showing the results of evaluating the melanogenesis inhibitory effects of arbutin and the arbutin ester compound obtained in Example 1, using mouse melanoma cells.

Evaluation 2: Evaluation of Melanogenesis Inhibitory Effect Using Mouse Melanoma Cells Mouse melanoma B16 cells ($3.6 \times 10^5$) were added to a 75 $cm^2$ culture flask containing 15 ml of D-MEM culture medium supplemented with 10% FCS, and incubated overnight at 37° C. under 5% carbon dioxide gas to adhere the cells. The culture medium was changed to 15 ml of 10% FCS-supplemented D-MEM culture medium containing one of 0.1% DMSO solutions of arbutin or 6-O-(10-undecylenoyl) arbutin obtained in Example 1-1 at various concentrations. The incubation was continued for two more days under the same conditions. The culture medium was again changed to 15 ml of the 0.1% DMSO solution-containing culture medium, and incubation was continued for two more days under the same conditions. After incubation, the cells were recovered, and the wet weight of the cells was measured. After the wet weight measurement, pellets of the cells were suspended in MilliQ water to a total volume of 700 μl. The cell suspension was subjected to ultrasonic disintegration for 15 minutes, and 700 μl of 6 N aqueous sodium hydroxide solution was admixed to completely dissolve the cells and extract melanin. The absorbance (405 nm) was then measured. This experiment was conducted three times to find the mean. The melanin production per cell was indicated as absorbance at 405 nm/cell wet weight (μg). The melanogenesis inhibitory effects of arbutin undecylenate or arbutin at each concentration was determined, with the melanin production per cell without addition of arbutin or arbutin undecylenate being taken as 100%. FIG. 4 shows the results.

FIG. 4 reveals that arbutin undecylenate exhibits about 100 times higher melanogenesis inhibitory effect than arbutin, when tested using melanoma cells.

Example 2-1

Figure 5:
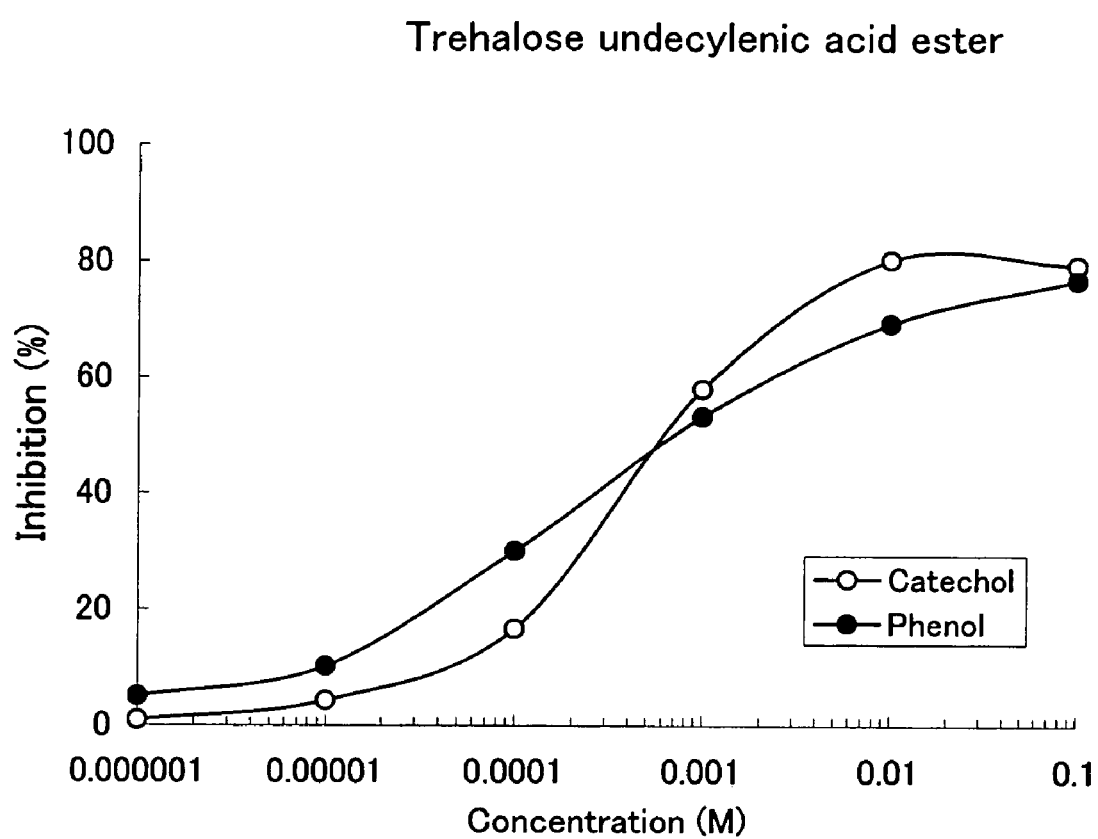
FIG. 5 is a graph showing the results of Examples 2-1 and 2-4 in which the tyrosinase inhibitory activity of undecylenic acid trehalose ester was tested using pyrocatechol and phenol, respectively, as substrates. "-○-Catechol" shows the results of the test using catechol as a substrate, and "-●-Phenol" shows the results of the test using phenol as a substrate.

The tyrosinase inhibitory activity of undecylenic acid sugar ester was measured using proline (Analytical Biochemistry, 179, 375-381, 1989). Specifically, 0.749 M L-proline (40 μl) dissolved in 0.1 M phosphate buffer at pH 7.5, 0.037 M pyrocatechol (40 μl) and a solution (1.41 ml) of trehalose undecylenic acid ester (Tre-Unde) at one of various concentrations were stirred in a cuvette for absorbance measurement. Subsequently, a solution (10 μl) of 350 μg/ml of tyrosinase (derived from mushroom, SIGMA) was added, and the absorbance change was measured with stirring for 3 minutes at 525 nm, confirming inhibition of tyrosinase. FIG. 5 shows the results.

Example 2-2

Figure 7:
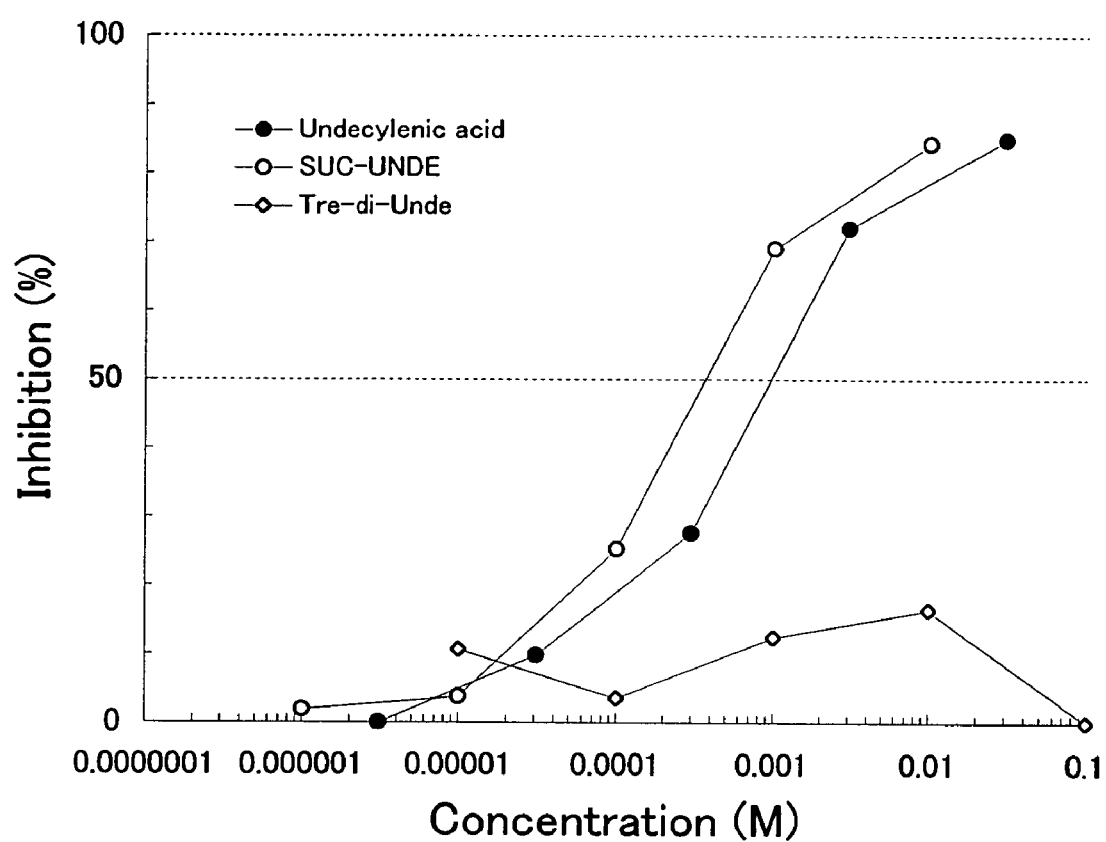
FIG. 7 is a graph showing the results of Examples 2-1 and 2-3 and Comparative Examples 2-2 in which tyrosinase inhibitory activity was tested using catechol as a substrate.

Undecylenic acid (Unde) was tested for tyrosinase inhibitory activity in the same manner as in Example 2-1, and confirmed to inhibit tyrosinase activity. FIG. 7. shows the results.

Example 2-3

Sucrose undecylenic acid ester (Suc-Unde) was tested for tyrosinase inhibitory activity in the same manner as in Example 2-1, and confirmed to inhibit tyrosinase activity. FIG. 7 shows the results.

Comparative Example 2-1

Figure 6:
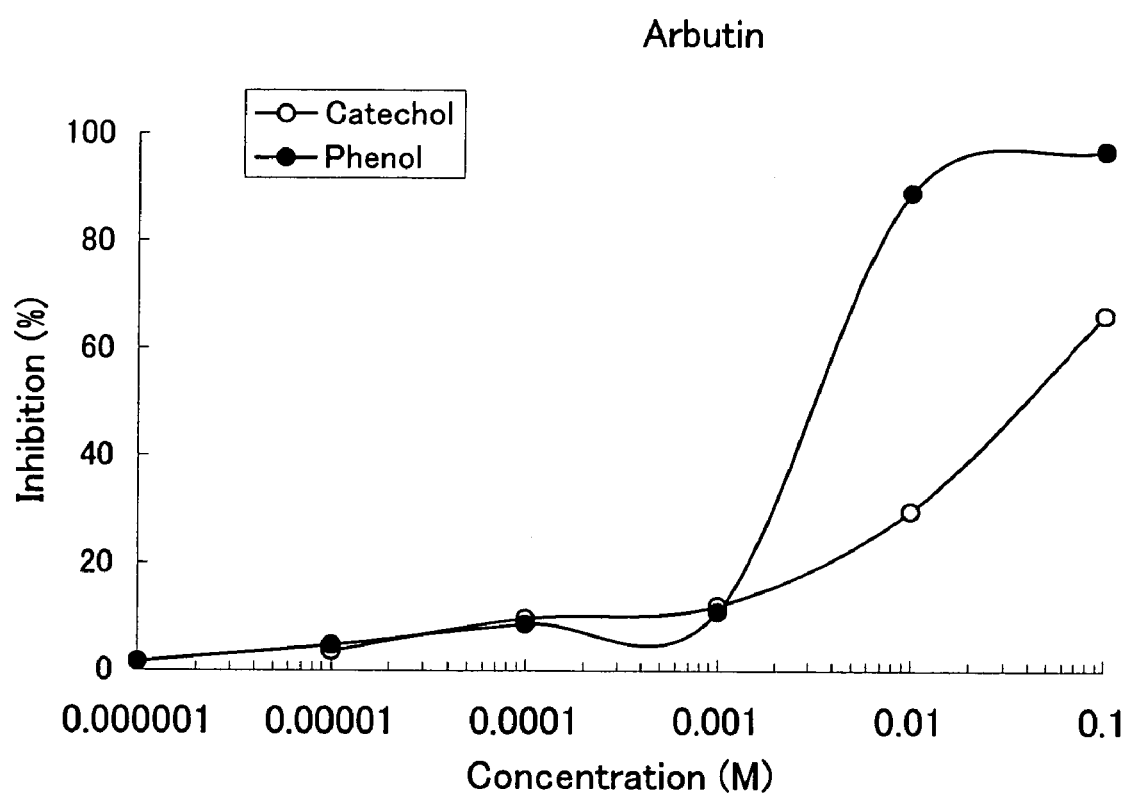
FIG. 6 is a graph showing the results of Comparative Examples 2-1 and 2-3 in which the tyrosinase inhibitory activity of arbutin was tested using catechol and phenol, respectively, as substrates. "-○-Catechol" shows the results of the test using catechol as a substrate, and "-●-Phenol" shows the results of the test using phenol as a substrate.

Arbutin was tested for tyrosinase inhibitory activity in the same manner as in Example 2-1 using pyrocatechol as a substrate, and confirmed to inhibit tyrosinase activity. FIG. 6 shows the results.

Comparative Example 2-2

Trehalose diundecylenic acid ester (Tre-di-Unde) was tested for tyrosinase inhibitory activity in the same manner as in Example 2-1, and confirmed to not inhibit tyrosinase activity. FIG. 7 shows the results.

Example 2-4

The tyrosinase inhibitory activity of an undecylenic acid sugar ester was determined using phenol as a substrate, by a modification of the method using pyrocatechol. Specifically, 40 µl of 0.749 M L-proline dissolved in 0.1 M phosphate buffer at pH 7.5, 40 µl of 0.037 M phenol and 1.41 ml of one of trehalose undecylenic acid ester (Tre-Unde) solutions at various concentrations were stirred in a cuvette for absorbance measurement. Subsequently, a solution (10 µl) of 350 µg/ml of tyrosinase (derived from mushroom, SIGMA) was added, and the absorbance change was measured with stirring for 15 minutes at 525 nm, confirming that the increase in absorbance was suppressed, i.e., tyrosinase was inhibited. FIG. 5 shows the results.

Example 2-5

Figure 8:
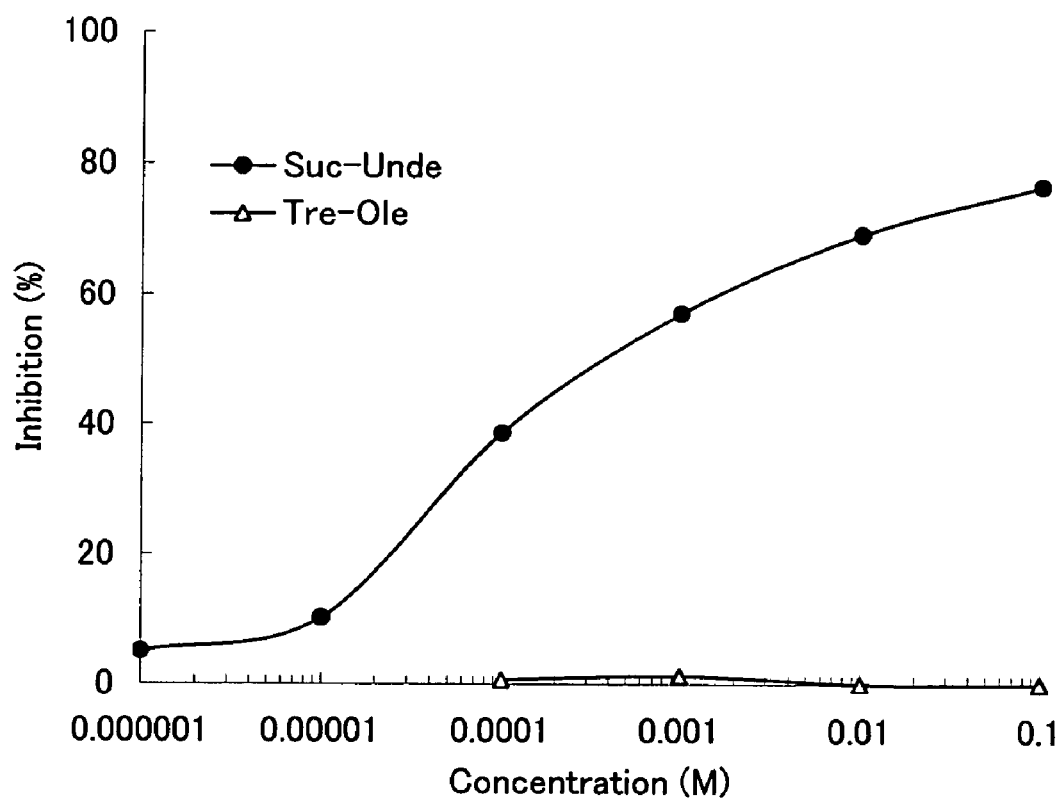
FIG. 8 is a graph showing the results of Example 2-5 and Comparative Example 2-4 in which tyrosinase inhibitory activity was tested using phenol as a substrate.
Figure 9:
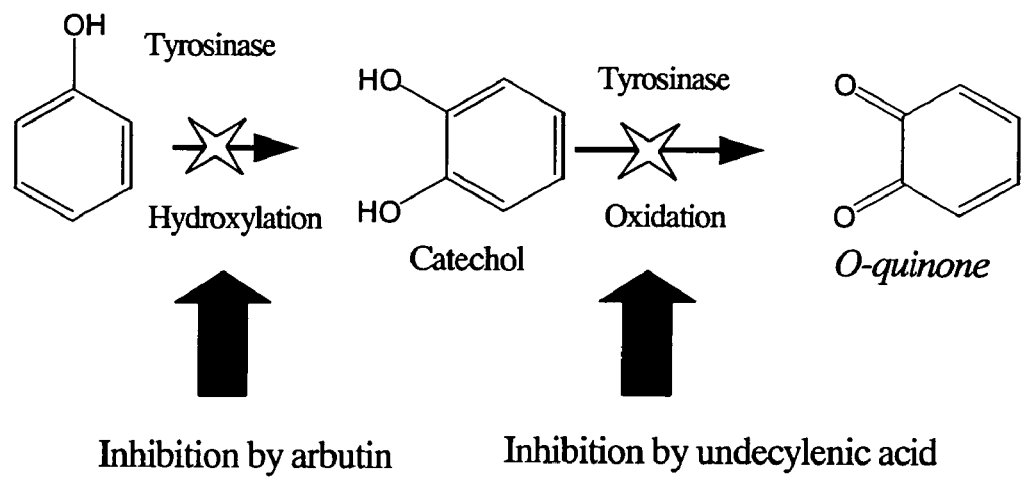
FIG. 9 is a scheme illustrating the tyrosinase inhibitory activity of arbutin and undecylenic acid. Arbutin chiefly inhibits the hydroxylation reaction of monophenol, whereas undecylenic acid inhibits the oxidation reaction of catechol.

Sucrose undecylenic acid ester (Suc-Unde) was tested for tyrosinase inhibitory activity in the same manner as in Example 2-4, and confirmed to inhibit tyrosinase activity. FIG. 8 shows the results.

Comparative Example 2-3

Arbutin was tested for tyrosinase inhibitory activity in the same manner as in Example 2-4, and confirmed to inhibit tyrosinase activity. FIG. 6 shows the results.

Comparative Example 2-4

Trehalose oleate (Tre-Ole) was tested for tyrosinase inhibitory activity in the same manner as in Example 2-4 using phenol as a substrate, and confirmed to not inhibit tyrosinase activity. FIG. 8 shows the results.

Example 3-1

Ascorbic acid and ascorbic acid derivatives were used as test substances for measuring tyrosinase activation promoting effects, using phenol as a substrate in the presence of proline.

Phenol is hydroxylated by tyrosinase, and at that time requires a hydrogen donor. The produced pyrocatechol is oxidized by tyrosinase to form an orthoquinone. The orthoquinone formed is quantitated in the presence of proline, to determine the tyrosinase activity.

Specifically, the measurement was carried out as follows. Forty microliters of 0.749 M L-proline dissolved in 0.1 M phosphate buffer at pH 7.5, 40 µl of 0.037 M phenol, and 1.41 ml of one of test substance solutions at various concentrations were stirred in a cuvette for absorbance measurement. A solution (10 µl) of 350 µg/ml of tyrosinase (derived from mushroom, SIGMA) was added, and the absorbance change was measured with stirring for 15 minutes at 525 nm, to determine the tyrosinase activity.

The tyrosinase activity promotion ratio was expressed as the percentage by which the tyrosinase activity was inhibited or promoted relative to that exhibited when the test substances had not been added. A tyrosinase activity promotion ratio of 100% indicates that the tyrosinase activity has increased twice as much as that exhibited when the test substances had not been added.

Of the test substances, the ascorbic acid was L-ascorbic acid (Wako Pure Chemical Ind. Ltd., Number: 016-04805), and the ascorbic acid derivatives were ascorbic acid-2-glucoside (Wako Pure Chemical Ind. Ltd., Number: 074-04581), ascorbic acid-2-phosphoric acid ester [ascorbic acid phosphoric acid ester magnesium salt (Wako Pure Chemical Ind. Ltd., Number: 013-12061)], and ascorbic acid-6-palmitate (Wako Pure Chemical Ind. Ltd., Number: 011-13662) represented by the following formulae.

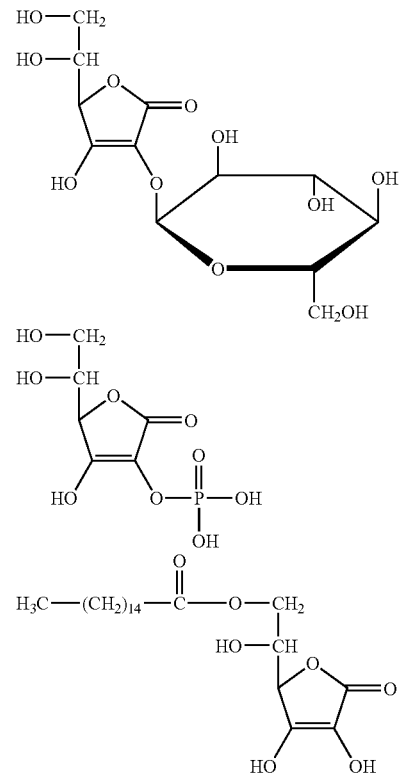

Figure 10:
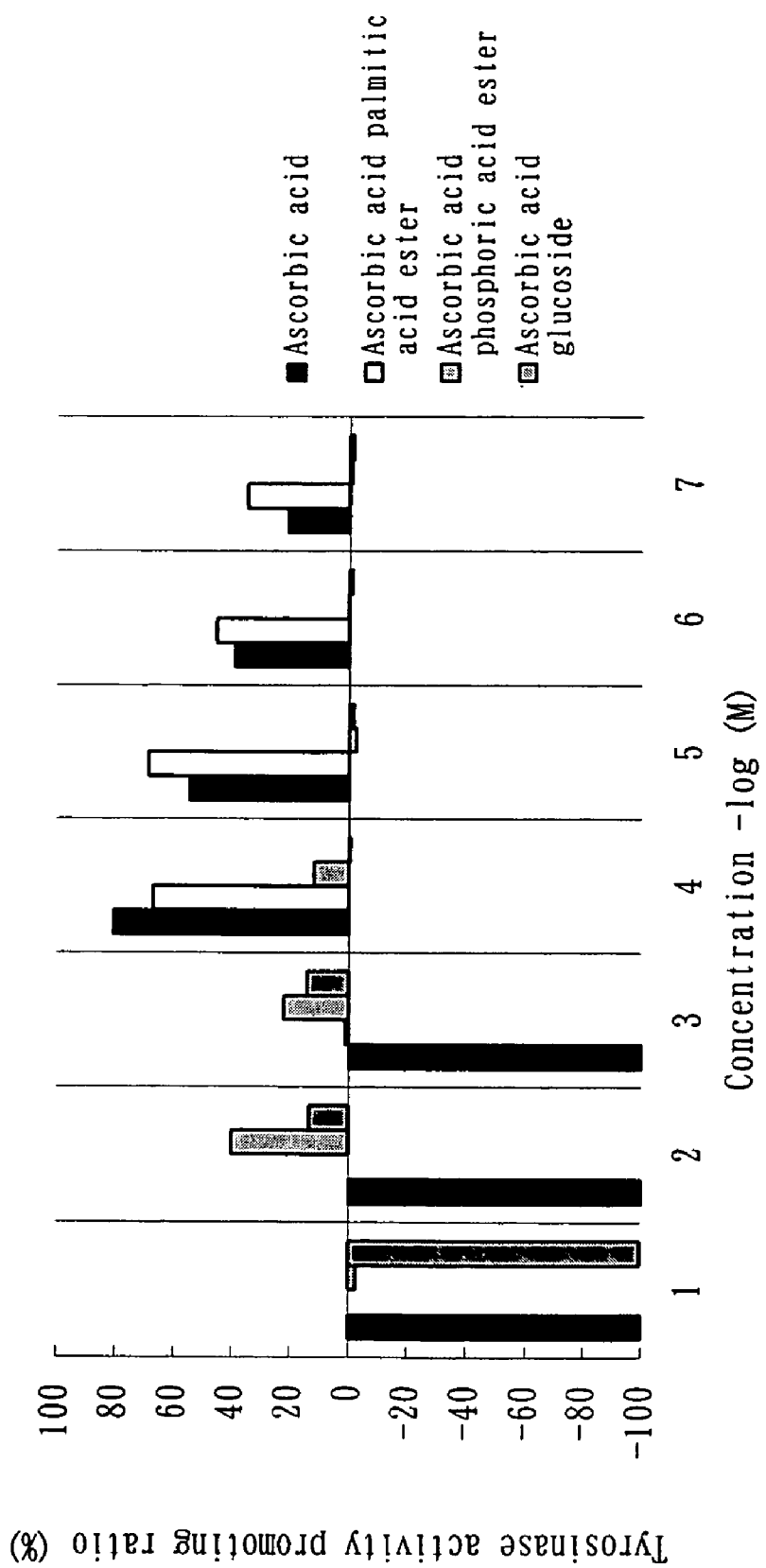
FIG. 10 is a graph showing the tyrosinase activity promoting ratios of ascorbic acid and ascorbic acid derivatives.

FIG. 10 shows the measurement results.

As shown in FIG. 10, ascorbic acid showed tyrosinase inhibitory activity at concentrations of $10^{-3}$ M to $10^{-1}$ M, but exhibited tyrosinase activity promoting effects at concentrations of $10^{-4}$ M and lower.

Ascorbic acid palmitic ester, a fatty acid ester of ascorbic acid, exhibited tyrosinase activity promoting effects at concentrations of $10^{-4}$ M and lower.

Ascorbic acid phosphoric acid ester and ascorbic acid glucoside showed tyrosinase activity promoting effect at concentrations of $10^{-2}$ M to $10^{-4}$ M.

Example 4-1

*Candida antarctica*-derived lipase type A (Chirazyme, L5, lyo:CAL-A) was added to a dimethylformamide (DMF) or dimethyl sulfoxide (DMSO) solution of 0.25 M sucrose and 1 M vinyl adipate to a concentration of 10 mg/ml, and a reaction was carried out at 40° C. for 24 hours to determine the ester conversion ratio. HPLC analysis of the reaction mixture confirmed that sucrose was converted to an ester substantially quantitatively. HPLC analysis conditions are shown below.

Column: TSK gel Amide-80
Eluate: Acetonitrile/water (3/1)
Detection: differential refraction Comparative Example 4-1

The procedure of Example 4-1 was followed except for using *Candida antarctica*-derived lipase type B (Chirazyme, L2, lyo:CAL-B) in place of *Candida antarctica*-derived lipase type A (Chirazyme, L5, lyo:CAL-A), to determine the ester conversion ratio.

Figure 11:
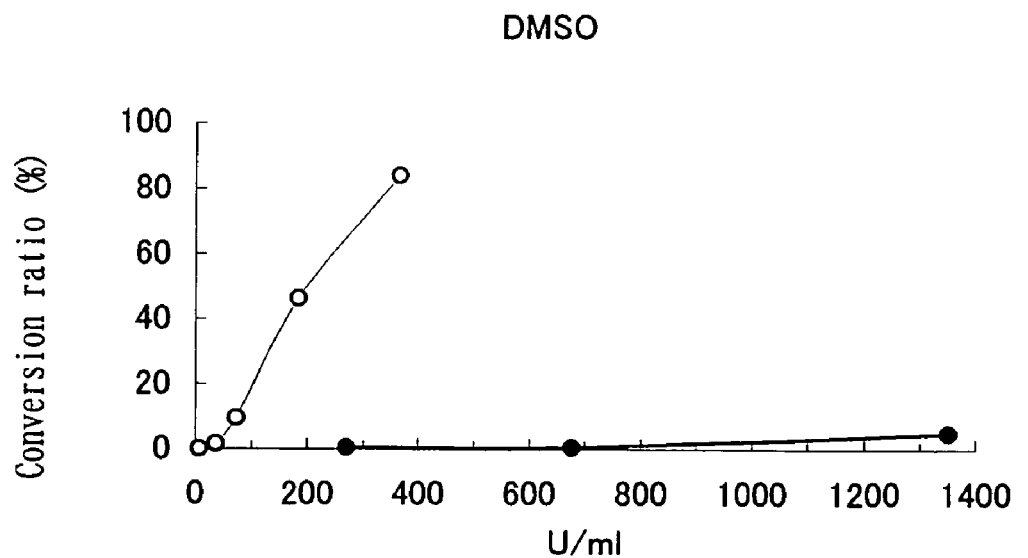
FIG. 11 is a set of graphs showing ester conversion ratios of reactions carried out by adding *Candida antarctica*-derived lipase type A (CAL-A) or *Candida antarctica*-derived lipase type B (CAL-B) to a DMF or DMSO solution of 0.25 M sucrose and 1 M divinyl adipate and maintaining the mixture at 40° C. for 24 hours. "○" shows the conversion ratio of the reactions using lipase type A, and "●" shows the conversion ratio of the reactions using lipase type B.
Figure 11:
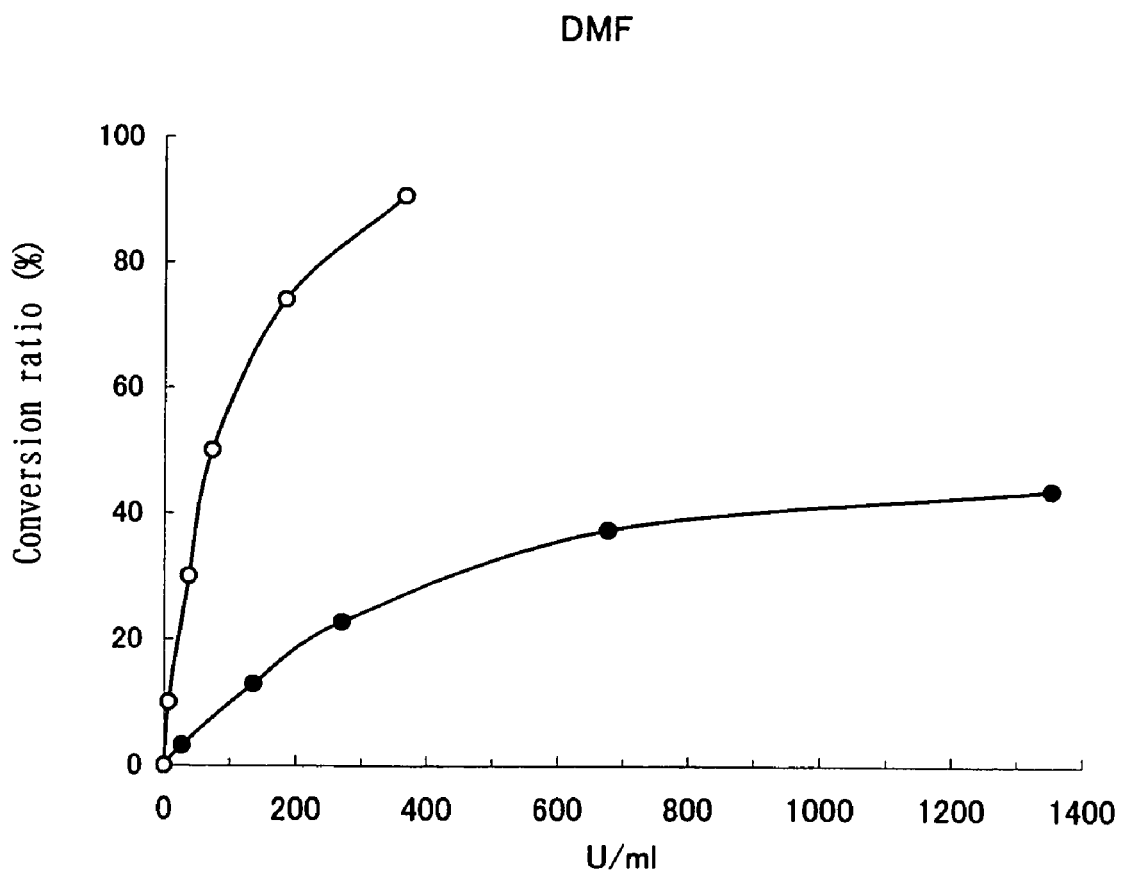

FIG. 11 shows the ester conversion ratios of Example 4-1 and Comparative Example 4-1. FIG. 11 clarifies that lipase type A shows higher activity than lipase type B in DMF and DMSO. In particular, the activity was remarkably high in DMSO.

Example 4-2

*Candida antarctica*-derived lipase type A (Chirazyme, L5, lyo) (10 mg/ml) was added to solutions of 0.125 M sucrose and 0.5 M vinyl adipate in mixtures consisting of DMF and DMSO in various proportions, followed by stirring at 30° C. for 24 hours to determine the sucrose ester conversion ratios. HPLC analysis of the reaction mixture confirmed that sucrose was converted to ester substantially quantitatively. HPLC analysis conditions are shown below.

Column: TSK gel Amide-80
Eluate: Acetonitrile/water (3/1)
Detection: Differential refraction Comparative Example 4-2

*Candida antarctica*-derived lipase type B (Chirazyme, L2, lyo) (10 mg/ml)) was added to solutions of 0.125 M sucrose and 0.5 M vinyl adipate in mixtures consisting of DMF and DMSO in various proportions, followed by stirring at 30° C. for 7 days, to determine the sucrose ester conversion ratios. HPLC analysis of the reaction mixtures confirmed that sucrose was converted to ester substantially quantitatively. HPLC analysis conditions were the same as in Example 4-2.

Figure 12:
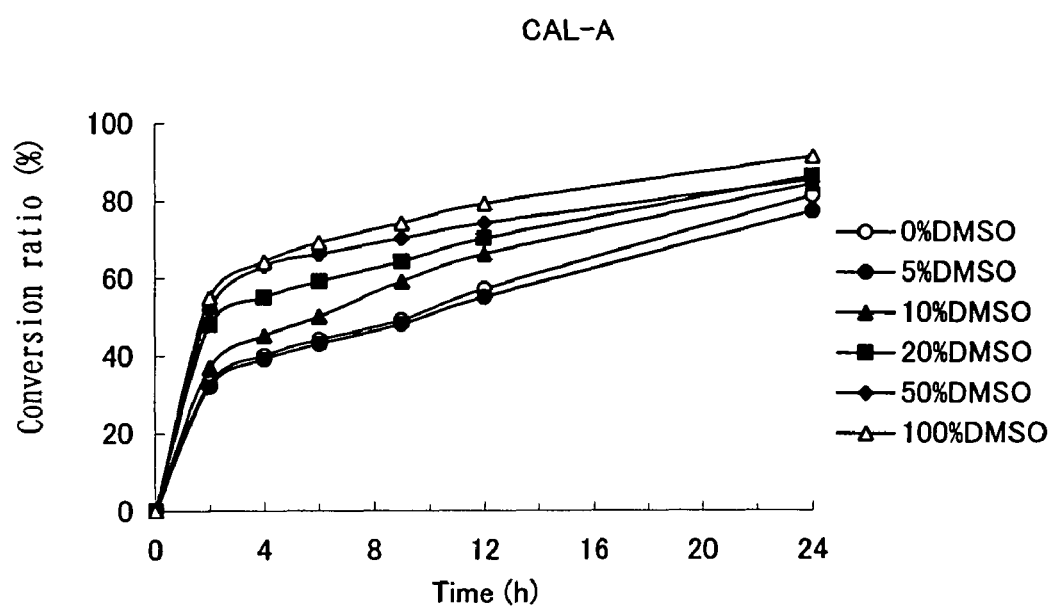
FIG. 12-A is a graph showing the sucrose ester conversion ratios of reactions carried out by adding *Candida antarctica*-derived lipase type A (CAL-A) to solutions of 0.125 M sucrose and 0.5 M divinyl adipate in mixed solvents consisting of DMF and DMSO in various proportions, followed by stirring at 30° C. for 24 hours.
Figure 12:
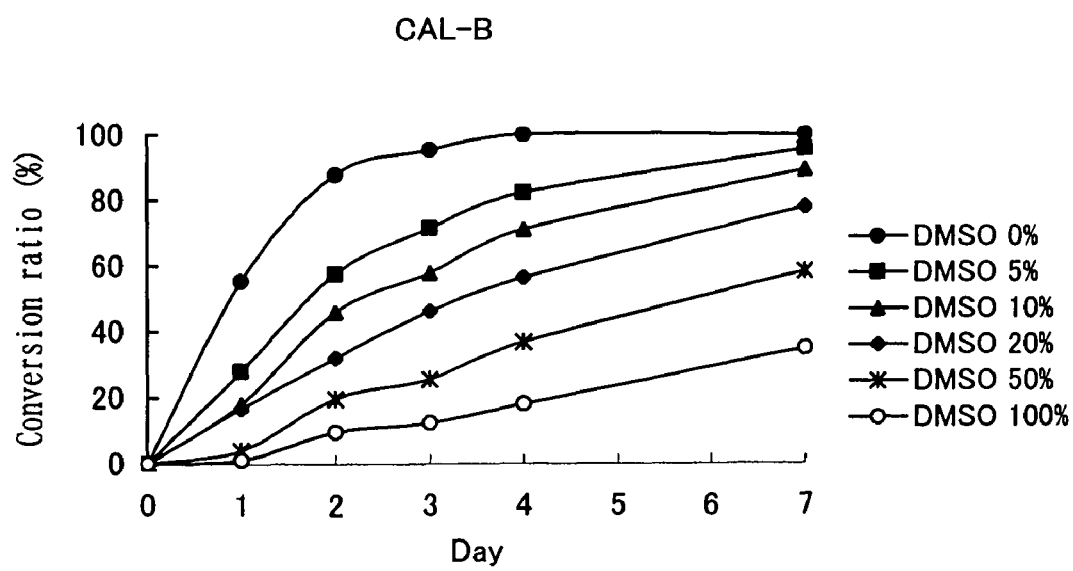

FIG. 12 shows the ester conversion ratios of Example 4-2 and Comparative Example 4-2. FIG. 12 clarifies that lipase type A (CAL-A) shows higher activity than lipase type B (CAL-B) in mixed solvents of DMF and DMSO. In particular, the greater the proportion of DMSO is, the greater the activity of lipase type A shows.

Example 4-3

Maltose (0.25 M) and divinyl adipate (1 M) were dissolved in dimethylformamide, dimethylsulfoxide or N-methylpyrrolidone (NMP), and 10 mg/ml of *Candida antarctica*-derived lipase type A (Chirazyme, L5, lyo: CAL-A) was added, followed by stirring at 40° C. for 24 hours to determine the ester conversion ratio. HPLC analysis of the reaction mixtures confirmed that sucrose was converted to ester substantially quantitatively. HPLC analysis conditions are shown below.

Column: TSK gel Amide-80
Eluate: Acetonitrile/water (3/1)
Detection: Differential refraction Comparative Example 4-3

The procedure of Example 4-3 was followed except for using *Candida antarctica*-derived lipase type B (Chirazyme, L2, lyo:CAL-B) in place of *Candida antarctica*-derived lipase type A (Chirazyme, L5, lyo:CAL-A), to determine the ester conversion ratio.

Figure 13:
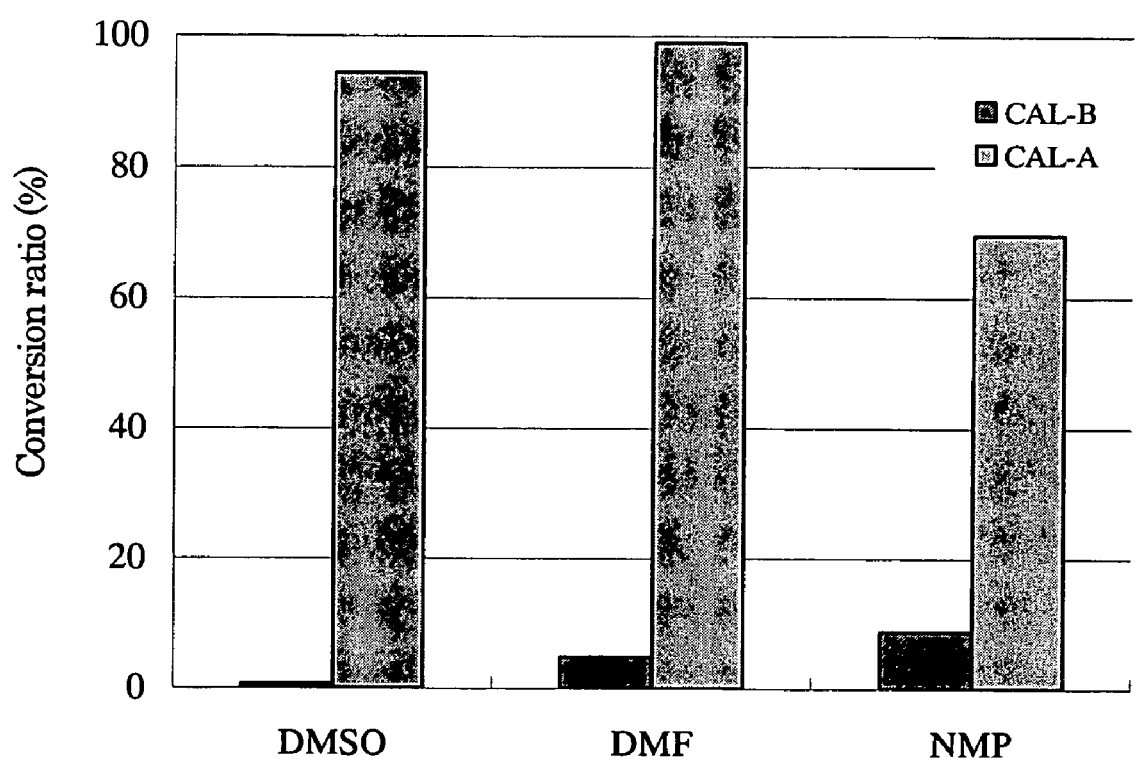
FIG. 13 is a graph showing the ester conversion ratios of reactions carried out by adding 10 mg/ml of *Candida Antarctica*-derived lipase type A (CAL-A) or *Candida antarctica*-derived lipase type B (CAL-B) to a solution of 0.25 M maltose and 1 M divinyl adipate in dimethylformamide (DMF), dimethylsulfoxide (DMSO) or N-methylpyrrolidone (NMP), followed by stirring at 40° C. for 24 hours.

FIG. 13 shows the ester conversion ratios of Example 4-3 and Comparative Example 4-3. FIG. 13 demonstrates that, when using maltose, type A exhibited remarkable reactivity in each aprotic organic solvent, unlike type B.

Example 4-4

*Candida antarctica*-derived lipase type A (Chirazyme, L5, lyo:CAL-A) (500 mg) was suspended in 150 ml of a dimethylformamide solution of 6.42 g (0.125 M) of sucrose and 10.7 g (0.5 M) of vinyl caproate. The enzymatic reaction mixture was stirred at 30° C. and 130 rpm for 24 hours. HPLC analysis of the reaction mixture was carried out under the same conditions as in Example 4-1 and confirmed that sucrose was converted to an ester substantially quantitatively.

TLC analysis of the reaction mixture confirmed that only one reaction product was formed. The insolubles were filtered out from the reaction mixture, and the filtrate was concentrated under reduced pressure using an evaporator, and added to a silica gel column (chloroform:methanol=12:1) to isolate and purify the ester to give 6.5 g of white crystals (yield: 79%). $^{13}$C NMR analysis confirmed formation of sucrose 2-caproic acid ester in which a caproic acid residue had been introduced to the 2-position of sucrose. $^{13}$C NMR (DMSO$_{d6}$): δ 88.70 (C1), 72.99 (C2), 70.05 (C3), 69.83 (C4), 72.56 (C5), 60.31 (C6), 61.14 (C1'), 104.23 (C2'), 75.3 (C3'), 82.63 (C4'), 73.75 (C5'), 62.32 (C6')

Example 4-5

*Candida antarctica*-derived lipase type A (Chirazyme, L5, lyo:CAL-A) (500 mg) was suspended in 150 ml of a dimethylformamide solution of 6.42 g (0.125M) of sucrose and 12.8 g (0.5M) of vinyl caprylate. The enzymatic reaction mixture was stirred at 30° C. and 130 rpm for 24 hours. HPLC analysis of the reaction mixture was carried out under the same conditions as in Example 4-1, confirming that sucrose was converted to an ester substantially quantitatively. The insolubles were filtered out from the reaction mixture, and the filtrate was concentrated and eluted with chloroform:methanol (12: 1, v/v) on a column packed with 100 g of silica gel, to give 6.8 g of white crystals (yield: 68%). $^{13}$C NMR analysis confirmed formation of sucrose 2-caprylic acid ester in which a caprylic acid residue had been introduced to the 2-position of sucrose.

$^{13}$C NMR (DMSO$_{d6}$): δ 88.71 (C1), 72.96 (C2), 70.05 (C3), 69.85 (C4), 72.55 (C5), 60.35 (C6), 61.13 (C1'), 104.25 (C2'), 75.27 (C3'), 82.62 (C4'), 73.80 (C5'), 62.39 (C6')

Example 4-6

*Candida antarctica*-derived lipase type A (Chirazyme, L5, lyo:CAL-A) (500 mg) was suspended in 150 ml of a dimethylformamide solution of 6.42 g (0.125 M) of sucrose and 15 g (0.5 M) of vinyl caprate. The enzymatic reaction mixture was stirred at 30° C. and 130 rpm for 3 days. HPLC analysis of the reaction mixture was carried out under the same conditions as in Example 4-1, confirming that sucrose was converted to an ester substantially quantitatively. The product was isolated in the same manner as in Example 4-5, to give 6.0 g of white crystals (yield: 64%). $^{13}$C NMR analysis confirmed formation of sucrose 2-capric acid ester in which a capric acid residue had been introduced to the 2-position of sucrose.

$^{13}$C NMR (DMSO$_{d6}$): δ 88.72 (C1), 72.94 (C2), 70.07 (C3), 69.86 (C4), 72.53 (C5), 60.34 (C6), 61.21 (C1'), 104.30 (C2'), 75.27 (C3'), 82.59 (C4'), 73.78 (C5'), 62.37 (C6')

Example 4-7

*Candida antarctica*-derived lipase type A (Chirazyme, L5, lyo:CAL-A) (500 mg) was suspended in 150 ml of a dimethylformamide solution of 6.42 g (0.125 M) of sucrose and 17 g (0.5 M) of vinyl laurate. The enzymatic reaction mixture was stirred at 30° C. and 130 rpm for 3 days. HPLC analysis of the reaction mixture was carried out under the same conditions as in Example 4-1, and confirmed that sucrose was converted to an ester substantially quantitatively. The product was isolated in the same manner as in Example 4-5, to give 6.9 g of white crystals (yield: 70%). $^{13}$C NMR analysis confirmed formation of sucrose 2-lauric acid ester in which a lauric acid residue had been introduced to the 2-position of sucrose.

$^{13}$C NMR (DMSO$_{d6}$): δ 88.80 (C1), 72.95 (C2), 70.10 (C3), 69.88 (C4), 72.55 (C5), 60.33 (C6), 61.19 (C1'), 104.30 (C2'), 75.31 (C3'), 82.62 (C4'), 73.83 (C5'), 62.35 (C6')

Example 4-8

*Candida antarctica*-derived lipase type A (Chirazyme, L5, lyo:CAL-A) (250 mg) was suspended in 25 ml of a dimethylsulfoxide solution of 2.14 g (0.25 M) of sucrose and 5 g (1 M) of divinyl adipate. The enzymatic reaction mixture was stirred at 30° C. and 130 rpm for 2 days. HPLC analysis of the reaction mixture was carried out under the same conditions as in Example 4-1, confirming that sucrose was converted to an ester substantially quantitatively. The product was isolated in the same manner as in Example 4-5, to give 2.6 g of white crystals (yield: 81%). $^{13}$C NMR analysis confirmed formation of sucrose 2-vinyl adipic acid ester in which a vinyl adipic acid residue had been introduced to the 2-position of sucrose.

$^{13}$C NMR (DMSO$_{d6}$): δ 88.70 (C1), 72.99 (C2), 70.05 (C3), 69.83 (C4), 72.56 (C5), 60.31 (C6), 61.14 (C1'), 104.28 (C2'), 75.30 (C3'), 82.63 (C4'), 73.75 (C5'), 62.32 (C6'), 23.49, 32.76, 33.18 (—CH$_2$—), 98.12, 141.26 (—C=C—), 170.33, 172.62 (—C=O)

Comparative Example 4-4

The procedure of Example 4-8 was followed except for using *Mucor javanicus*-derived lipase (lipase M), *Aspergillus niger*-derived lipase (lipase A') or *Candida cylindracea*-derived lipase (lipase AY) in place of *Candida antarctica*-derived lipase type A (lipase A), to determine the sucrose ester conversion ratio.

Table 4-1 showed the ratio of conversion to sucrose 2-vinyl adipic acid ester achieved by using each lipase in Example 4-8 and Comparative Example 4-4.

TABLE 4-1

| Enzyme | Source | Conversion ratio (in DMSO) |
| --- | --- | --- |
| Lipase A | Candida antarctica | 62.0% |
| Lipase M | Mucor javanicus | 11.4% |
| Lipase A' | Aspergillus niger | 17.6% |
| Lipase AY | Candida cylindracea | 6.7% |

As shown in Table 4-1, it was confirmed that *Candida antarctica*-derived lipase type A achieves a remarkably higher conversion ratio than lipases derived from other microorganisms.

INDUSTRIAL APPLICABILITY

The present invention provides a tyrosinase activity controlling agent comprising as an active ingredient a compound that has tyrosinase inhibiting or promoting activity, and an external preparation comprising the controlling agent. The present invention further provides a process for producing the compound.

Specifically, the present invention provides a novel arbutin ester compound that has tyrosinase inhibitory activity, a tyrosinase inhibitor comprising the compound as an active ingredient, and an external preparation comprising the inhibitor.

Further, the present invention provides a tyrosinase inhibitor comprising, as an active ingredient, undecylenic acid, salt(s) thereof and/or ester derivative(s) thereof, and an external preparation comprising the tyrosinase inhibitor.

Furthermore, the present invention provides a tyrosinase activity promoter comprising, as an active ingredient, ascorbic acid and/or derivative(s) thereof, and an external preparation comprising the tyrosinase activity promoter.

Also provided is a process for producing an ester using an enzyme, the process being applicable to the production of the tyrosinase inhibitor or promoter.

The novel arbutin ester compound of the present invention has higher tyrosinase inhibitory activity than arbutin, due to the introduction of a hydrophobic group to the hydroxyl group at the 6-position of arbutin. The introduction of the hydrophobic group also improves the skin absorption properties of the compound. Moreover, the compound has antimicrobial activity against a wide variety of microbes, presumably based on the sugar ester structure, radical eliminating capacity, presumably due to the phenolic hydroxyl group, and surface activating effect, presumably based on the hydrophobicity of the ester moiety and the hydrophilicity of the arbutin moiety.

The tyrosinase inhibitor comprising the compound as an active ingredient and the external preparation comprising the inhibitor exhibit remarkable tyrosinase activity inhibitory effect, and can be effectively used for external preparations for the skin, cosmetic preparations for skin whitening, and additives or the like in the cosmetic and medical fields.

One embodiment of the present invention is based on the finding that esters of undecylenic acid and disaccharides greatly inhibit tyrosinase activity by a mechanism different from that of arbutin. Specifically, tyrosinase catalyzes hydroxylation of monophenol to 1,2-diphenol (catechol) and oxidation of catechol to o-quinone, and arbutin efficiently inhibits the hydroxylation of monophenol, whereas undecylenic acid, salts thereof and ester derivatives thereof inhibit the oxidation of catechol.

In particular, ester derivatives of undecylenic acid have improved skin absorption properties due to the introduction of a hydrophobic group. Further, the ester derivatives have antimicrobial activity against a wide variety of microbes, presumably due to the undecylenic acid group, and surface activating effect, presumably due to the hydrophobicity of the ester moiety and hydrophilicity of the arbutin moiety.

The tyrosinase inhibitor comprising, as an active ingredient, undecylenic acid, salt(s) thereof and/or ester derivative(s) thereof, which have the above properties, and the external preparation comprising the inhibitor can be effectively used for cosmetic preparations, cosmetic preparations for skin whitening, additives and the like in the cosmetic or medical fields.

Another embodiment of the present invention is based on the finding that ascorbic acid and ascorbic acid derivatives have excellent tyrosinase activity promoting effect and excellent melanogenesis promoting effects.

Despite that ascorbic acid and ascorbic acid derivatives have been hitherto used as melanogenesis inhibitors, the present inventors discovered that ascorbic acid and ascorbic acid derivatives have tyrosinase activity promoting and melanogenesis promoting effects.

Ascorbic acid and ascorbic acid derivatives are safe and can be produced at low cost.

The tyrosinase activity promoter comprising, as an active ingredient, ascorbic acid and/or ascorbic acid derivative(s), which have the above advantages, and the external preparation comprising the promoter are highly safe, can be produced at low cost, and have excellent tyrosinase activating effect and excellent melanogenesis promoting effects.

The tyrosinase activity promoter and external preparation comprising the promoter are useful in the cosmetic and medical fields as, for example, a pharmaceutical preparation or external preparation for the hair for preventing or alleviating hair graying; a pharmaceutical or external preparation for the skin for darkening the skin or for treating vitiligo of the skin; and the like.

The present invention also provides an enzymatic process for producing an ester, the process being capable of using a hydroxyl-containing compound as a starting material and capable of producing an ester in high yield.

Enzymatic transesterification reactions have hitherto been carried out mainly in hydrophobic organic solvents, whereas according to the present invention, enzymatic esterification can be carried out in an aprotic organic solvent, such as DMSO, when using a specific enzyme. This makes it possible to obtain an ester in high yield, in a solvent in which hydroxyl-containing compounds are highly soluble, using a hydroxyl-containing compound as a starting material.

Further, when using sucrose as the hydroxyl-containing compound in the process of the present invention, an ester in which the hydroxyl group at the 2-position of sucrose is specifically esterified is obtained.

Sucrose fatty acid esters have hitherto been obtained mainly as mixtures of mono-, di- and triesters in which the primary hydroxyl groups at the 1'-, 6- and/or 6'-positions are esterified. In the present invention, a sucrose monoester compound, in which the secondary hydroxyl group at the 2-position is specifically esterified, can be obtained in high yield.

The sucrose ester obtained by the process of the present invention has high hydrophilicity, and excellent characteristics in terms of solubility, emulsifiability, stability, etc. and can be suitably used in foods, cosmetics, shampoos, hair rinses, medicines, agricultural chemicals, detergents and other fields, as an emulsifier, surfactant or the like.

The process of the present invention is an excellent means for ester production using as a starting material a hydroxyl-containing compound, which is sparingly soluble in hydrophobic organic solvents; and production of an ester that is difficult to produce synthetically and/or that necessitates a selective enzymatic reaction.

The invention claimed is:

1. An arbutin ester compound represented by formula (1):

Formula (1)

$$\text{CH}_2\text{OCO—Ra}$$

[structure of arbutin ester with sugar ring bearing OH, OH, OH groups and $O$-phenyl-OH substituent]

wherein Ra is selected from the group consisting of:
  $R_1$—CH=CH$_2$, wherein $R_1$ is a single bond, an unsubstituted alkyl group or an arylene group;

$$R_1\overset{\text{CH}_3}{\text{C}}=\text{CH}_2,$$

wherein $R_1$ is a single bond, an alkyl group or an arylene group;
  $R_1$—COOCH=CH$_2$, wherein $R_1$ is a single bond, an alkyl group or an arylene group;
  $R_1$—COOH, wherein $R_1$ is a single bond, an alkyl group or an arylene group;
  $R_1$—COO—$R_2$, wherein $R_1$ is a single bond, an alkyl group or an arylene group; and $R_2$ is an alkyl group or an aryl group; and
  $R_1$—C(CH$_3$)$_3$, wherein $R_1$ is a single bond, an alkyl group or an arylene group.

2. A process for producing an arbutin ester compound, comprising the step of carrying out an esterification reaction of arbutin with a carboxylic acid compound represented by one of formulae (11) to (15) or (17):

A-OCO—$R_1$—CH=CH$_2$          Formula (11)

wherein A is hydrogen or a substituted or unsubstituted alkyl or vinyl group; and $R_1$ is a single bond, an unsubstituted alkyl group or an arylene group;

A-OCO—$R_1$—C(CH$_3$)=CH$_2$          Formula (12)

wherein A is hydrogen or a substituted or unsubstituted alkyl or vinyl group; and $R_1$ is a single bond, an alkyl group or an arylene group;

A-OCO—$R_1$—COOCH=CH$_2$          Formula (13)

wherein A is hydrogen or a substituted or unsubstituted alkyl or vinyl group; and $R_1$ is a single bond, an alkyl group or an arylene group;

A-OCO—$R_1$—COOH          Formula (14)

wherein A is hydrogen or a substituted or unsubstituted alkyl or vinyl group; and $R_1$ is a single bond, an alkyl group or an arylene group;

$$A\text{-}OCO\text{-}R_1\text{-}COO\text{-}R_2 \quad \text{Formula (15)}$$

wherein A is hydrogen or a substituted or unsubstituted alkyl or vinyl group; $R_1$ is a single bond, an alkyl group or an arylene group; and $R_2$ is an alkyl group or an aryl group;

$$A\text{-}OCO\text{-}R_1\text{-}C(CH_3)_3 \quad \text{Formula (17)}$$

wherein A is hydrogen or a substituted or unsubstituted alkyl or vinyl group; and $R_1$ is a single bond, an alkyl group or an arylene group.

3. The process according to claim 2, wherein the esterification is carried out in the presence of an enzyme catalyst.

4. The process according to claim 2, wherein the esterification is carried out in the presence of a chemical catalyst.

5. The process according to claim 2, wherein the esterification is carried out while performing a dehydration treatment.

6. The process according to claim 2, wherein the esterification reaction step is followed by the steps of:
    extracting and isolating unreacted carboxylic acid derivative(s) from the esterification reaction mixture with a nonpolar organic solvent; and subsequently,
    adding excess water to extract and isolate unreacted arbutin and to precipitate the arbutin ester compound.

7. A composition comprising an arbutin ester compound according to claim 1 and a suitable carrier.

8. An external preparation for the skin comprising the composition according to claim 7.

9. The arbutin ester compound of claim 1, wherein —Ra is selected from the group consisting of:
    —$R_1$—CH=$CH_2$, wherein $R_1$ is a single bond, an unsubstituted alkyl group or an arylene group;
    —$R_1$—C($CH_3$)=$CH_2$, wherein $R_1$ is a single bond, an alkyl group or an arylene group;
    —$R_1$—COOCH=$CH_2$, wherein $R_1$ is a single bond, an alkyl group or an arylene group; and
    —$R_1$—C($CH_3$)$_3$, wherein $R_1$ is a single bond, an alkyl group or an arylene group.

10. The arbutin ester compound of claim 1, wherein —Ra is selected from the group consisting of:
    —$R_1$—CH=$CH_2$, wherein $R_1$ is a single bond or an unsubstituted alkyl group having 1 to 16 carbon atoms;
    —$R_1$—C($CH_3$)=$CH_2$, wherein $R_1$ is a single bond;
    —$R_1$—COOCH=$CH_2$, wherein $R_1$ is an alkyl group having 1 to 16 carbon atoms; and
    —$R_1$—C($CH_3$)$_3$, wherein $R_1$ is a single bond.

11. An arbutin ester compound selected from the group consisting of 6-O-acryloyl arbutin, 6-O-methacryloyl arbutin, 6-O-vinyladipoyl arbutin, 6-O-adipoyl arbutin, 6-O-methyladipoyl arbutin, 6-O-decenoyl arbutin, 6-O-oleoyl arbutin, 6-O-pivaloyl arbutin, 6-O-butanoyl arbutin, 6-O-laruoyl arbutin, 6-O-stearoyl arbutin, and 6-O-(10-undecylenoyl) arbutin.

12. The arbutin ester compound of claim 11, wherein the compound is 6-O-(10-undecylenoyl)arbutin.

13. A composition comprising an arbutin ester compound of claim 11 and a suitable carrier.

14. An external preparation for the skin comprising the composition of claim 13.

* * * * *

UNITED STATES PATENT AND TRADEMARK OFFICE
CERTIFICATE OF CORRECTION

PATENT NO. : 7,754,864 B2
APPLICATION NO. : 10/530789
DATED : July 13, 2010
INVENTOR(S) : Tokiwa et al.

It is certified that error appears in the above-identified patent and that said Letters Patent is hereby corrected as shown below:

Title Page, Item (74), please delete "Marten" and insert therefore, --Martens--.

Title Page, at page 2 under "Other Publications," right column, line 4, please delete "Acrylation" and insert therefore, -- Acylation--.

Title Page, at page 2 under "Other Publications," right column, line 5, please delete "Infuluence" and insert therefore, --Influence--.

At column 2, line 47, please delete "*Rucus*" and insert therefore, --*Ruscus*--.

At column 2, line 52 (approx.), please delete "Hydnaceae," and insert therefore, --Hypnaceae,--.

At column 5, line 36 (approx.), please delete "repr" and insert therefore, --represented by formula (7):,--.

At column 5, line 37 (approx.), above " 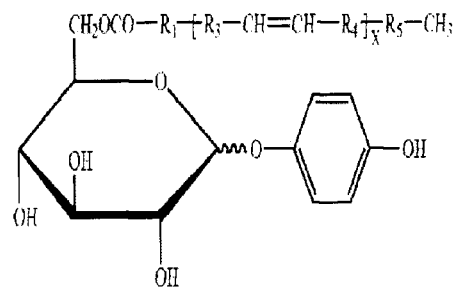 " please add -- Formula (7)--.

At column 7, line 12, please delete "1 to 6." and insert therefore, --1 to 6;--.

At column 7, line 28, please delete "group;" and insert therefore, --group.--.

Signed and Sealed this
Twenty-second Day of March, 2011

David J. Kappos
*Director of the United States Patent and Trademark Office*

CERTIFICATE OF CORRECTION (continued)
U.S. Pat. No. 7,754,864 B2

At column 10, line 5, please delete "linolic" and insert therefore, --linoleic--.

At column 11, line 18, please delete "*anterctica*" and insert therefore, --*antarctica*--.

At column 11, line 31, please delete "*anterctica*" and insert therefore, --*antarctica*--.

At column 21, line 59, please delete "hydrolyzates" and insert therefore, --hydrolysates--.

At column 22, line 35, please delete "linolic" and insert therefore, --linoleic--.

At column 25, line 27, please delete "7.76." and insert therefore, --7.76,--.

At column 25, line 43 (approx.), please delete "decenoate" and insert therefore, --decanoate--.

At column 25, line 47 (approx.), please delete "butayl" and insert therefore, --butyl--.

At column 26, line 4, after "(1H, q, —CH=)" please add --.--.

At column 26, line 29, please delete "7.76." and insert therefore, --7.76,--.

At column 26, line 45 (approx), please delete "decenoate" and insert therefore, --decanoate--.

At column 26, line 48 (approx.), please delete "butayl" and insert therefore, --butyl--.

At column 27, line 29, after "find that" please delete "the".

At column 27, line 42 (approx.), please delete "*anterctica*" and insert therefore, --*antarctica*--.

At column 28, line 11, please delete "$\mu l/ml$" and insert therefore, --$\mu g/ml$--.

At column 38, line 23 (Claim 11), please delete "laruoyl" and insert therefore, -- lauroyl--.